United States Patent [19]

Smith

[11] Patent Number: 5,286,651
[45] Date of Patent: Feb. 15, 1994

[54] DETERMINING COLLECTIVE FLUID INCLUSION VOLATILES COMPOSITIONS FOR INCLUSION COMPOSITION MAPPING OF EARTH'S SUBSURFACE

[75] Inventor: Michael P. Smith, Tulsa, Okla.

[73] Assignee: Amoco Corporation, Chicago, Ill.

[21] Appl. No.: 60,485

[22] Filed: May 11, 1993

Related U.S. Application Data

[63] Continuation of Ser. No. 398,341, Aug. 24, 1989, abandoned.

[51] Int. Cl.$^5$ .................... G01N 33/24; G01V 5/00
[52] U.S. Cl. ................................ 436/32; 73/153;
73/863.21; 250/256; 250/281; 250/282;
250/307; 422/64; 422/83; 436/25; 436/29;
436/31; 436/43; 436/173
[58] Field of Search .............. 73/153, 863.21, 864.91;
250/256, 281, 282, 307; 422/64, 83; 436/25, 29,
31, 32, 43, 173

[56] References Cited

U.S. PATENT DOCUMENTS

| | | | |
|---|---|---|---|
| 3,524,346 | 7/1968 | Schmidt | 73/153 |
| 3,624,420 | 11/1971 | Krutz et al. | 250/281 X |
| 3,866,041 | 2/1975 | Attia | 250/430 X |
| 3,918,913 | 11/1975 | Stevenson et al. | 436/43 X |
| 4,209,697 | 6/1980 | Renner et al. | 250/282 |
| 4,507,555 | 3/1985 | Chang | 250/281 |
| 4,573,354 | 3/1986 | Voorhees et al. | 73/863.21 X |
| 4,814,614 | 3/1989 | Tsui | 250/301 |
| 4,856,351 | 8/1989 | Smith et al. | 73/863.21 |
| 5,224,658 | 7/1993 | Smith | 73/863.21 |

FOREIGN PATENT DOCUMENTS 1249617  8/1986  U.S.S.R. .

OTHER PUBLICATIONS

C. Barker et al., "Analysis of Gases in Individual Fluid Inclusions in Natural Minerals Using a Dual Mass Spectrometer System" *Analyst* 1992, 117, 1407–1411.

Sommer, M. A., "Volatiles $H_2O$, $Co_2$, and CO in Silicate Melt Inclusions in Quartz Phenocryts from Rhyolitic Bandelier Air-Fall and Ash-Flow Tuff, New Mexico" *J. Geology*, 1977, 85, pp. 423–432.

Barker, C. et al., "Mass Spectrometric Determination of Gases in Individual Fluid Inclusions in Natural Minerals", 1986, *Anal. Chem.*, 58, 1330–1333.

Andrawes, F. F. et al., "Release and Analysis of Gases from Geological Samples", *Am. Mineral.*, 1979, 64, 453–463.

Reynolds, W. E., et al., "A Computer Operated Mass Spectrometer System", *Anal. Chem.* 1970, 42, 1122–1129.

Kaliuzhny, V. A., "Fundamentals of Science on Mineral Forming Fluids," Kiev, Naukova Dumka Publishers, Academy of Sciences of the Ukranian SSR Institute for Geology and Geochemistry of Combustible Minerals, 1982 pp. 83, 88–89, 92–93.

Horsfield, et al., "Geothermometry and Geochemistry of Aqueous and Oil-Bearing Fluid Inclusions from Fateh Field Dubai," Org. Geochem., vol. 6, pp. 733–740, 1984.

Pagel, et al., "Fluid Inclusions in Oil and Gas-Bearing Sedimentary Formations," First Institute French du Petrole, et al., Therm Modeling in Sediment Basin Explore RES Conference Proceedings, No. 44, pp. 565–583 (1986).

(List continued on next page.)

*Primary Examiner*—James C. Housel
*Assistant Examiner*—Arlen Soderquist
*Attorney, Agent, or Firm*—Richard A. Kretchmer

[57] ABSTRACT

A collective fluid inclusions volatiles sample is released from each of a plurality of sedimentary rock samples and analyzed as it is being released to determine composition thereof. Compositions are used for mapping the earth's subsurface. The sample is released by an automated crushing mechanism and analyzed by a system of concurrently operated mass spectrometers each scanning a specific set of mass to charge ratio responses.

15 Claims, 25 Drawing Sheets

OTHER PUBLICATIONS

Roedder, E., "Fluid Inclusion Evidence on the Environments of Sedimentary Diagenesis, A Review," SEPM Special Publication No. 26, pp. 89–107 (1979).

Barker, Colin G. "Volatile Content of Rocks and Minerals with Special Reference to Fluid Inclusions," Dept. of Geology, University of Texas, Austin, TX. Abstract.

Barker, et al. (1973) "Mass Spectrometric Analysis of the Volatiles Released by Heating or Crushing Rocks," ASTM Publication STP 539, pp. 56–70.

Barker, et al. "Gas Adsorption on Crushed Quartz and Basalt," Geochimica et Cosmochimica Acta 39, 212–218 (1975).

Burruss, R. C. (1981) "Hydrocarbon Fluid Inclusions in Studies of Sedimentary Diagenesis," from Hollister et al. (eds) *Short Course in Fluid Inclusions: Applications to Petrology*, vol. 6, Mineralogical Assoc. of Canada, pp. 138–156.

Gibson, Jr., E. A. (1973) "Thermal Analysis-mass Spectrometer Computer System and its Application to the Evolved Gas Analysis of Green River Shale and Lunar Soil Samples," Thermochim. Acta, 5, 243–255. (1973).

Gurevich, et al. (1975) "Carousel Sample Holder with Magnetic Rotational Drive."

Haszeldine et al. (1984) "Dating Diagenesis in a Petroleum Basin, a New Field Inclusion Method." *Nature* vol. 307, pp. 354–357.

Kalyuzhnyi, V. A. and Svoren', I. M., (1978) Abstract: "Rational Method of Release and Analysis of Gas Components of Inclusions during Mechanical Destruction of Minerals."

Kranz, R. L. (1968) "Participation of Organic Compounds in the Transport of Ore Metals in Hydrothermal Solution" Trans. Instn. Min. Metall. 77, B–26–36.

Kvenvolden, et al. (1971) "Fluid Inclusions in Quartz Crystals from South-west Africa" Geochim. Cosmochim. Acta 35, 1209–1229.

Mercer, P. D. (1967) "Analysis of the Gases Released on Cleaving Muscovite Mica in Ultrahigh Vacuum and of Gases which remain Adsorbed on the Freshing Cleaved Surface", Vacuum. 17, 267–270.

Ohba, T. (1988) "Precise Determination of Hydrogen and Oxygen Isotope Ratios of Water in Fluid Inclusions of Quartz and Halite," Geochem. J. vol. 22, No. 2 pp. 55–68.

Roedder, E. (1984) "Reviews in Mineralogy," vol. 12 Fluid Inclusions. pp. 122–124 and 126–136.

Shepherd, et al. (1985) "A Practical Guide to Fluid Inclusion Studies." Blackie & Sons, Glasgow, Great Britain, pp. 172–176 and 219–222.

Todd, B. J. (1956) "Mass Spectrometer Analysis of Gases in Blisters in Glass," Soc. Glass Tech. Trans., 40, 32T–38T.

Vochten, R., Esmans, E. and Vermeirsch, W., 1977. "Study of the Solid and Gaseous Inclusions in the Fluorites from Wolsendorf (Bavaria, F. R. of Germany) and Margnac (Haute Vienne, France) by Microprobe and Mass Spectrometry," Chem. Geol., 20: 253–264.

Gibson, Jr., E. K. and Johnson, S. M. (1971) "Thermogravimetric Quadrupole Mass Spectrometric Analysis of Geochemical Samples," Thermochim. Acta. 5, 49–56.

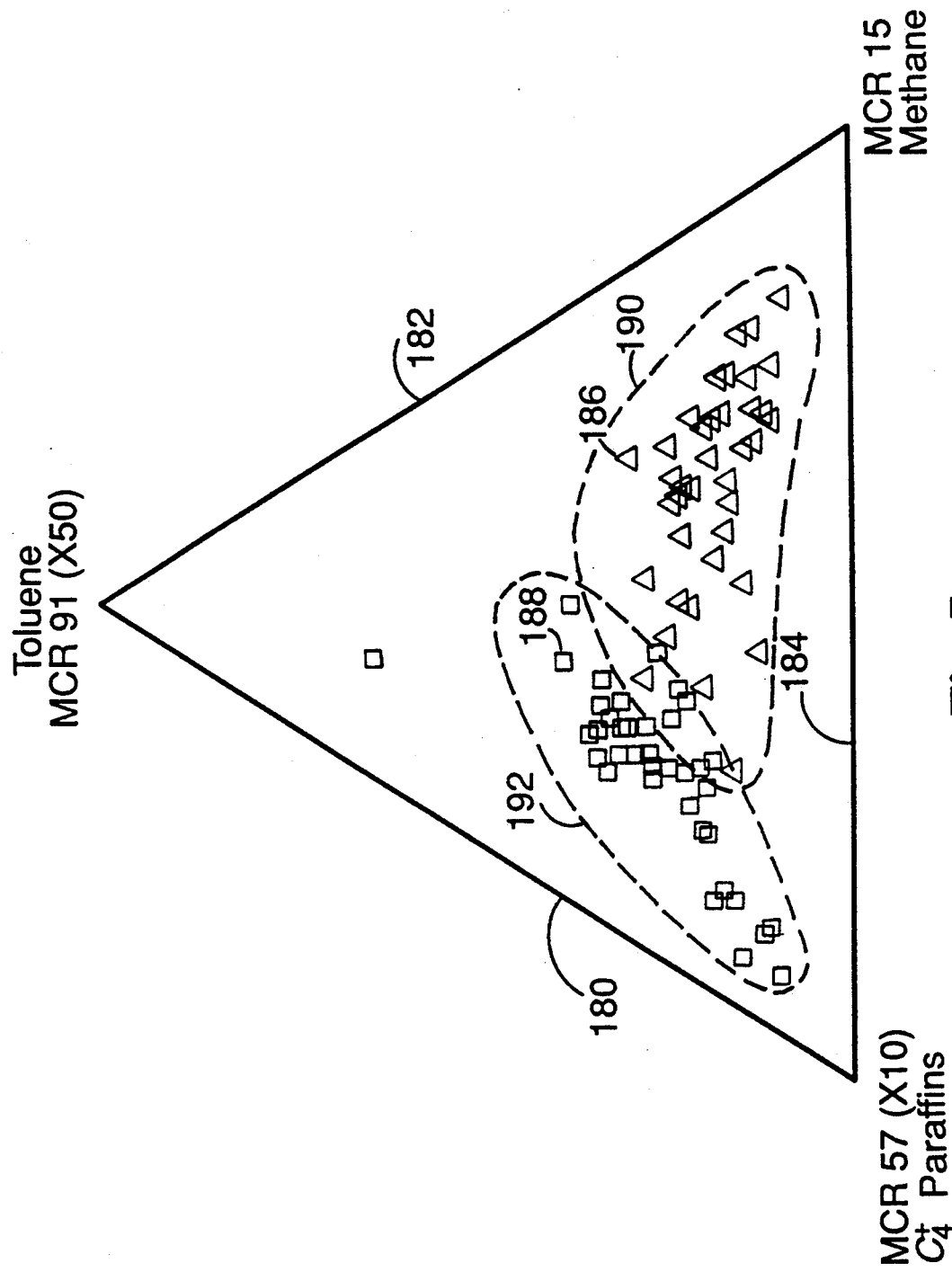

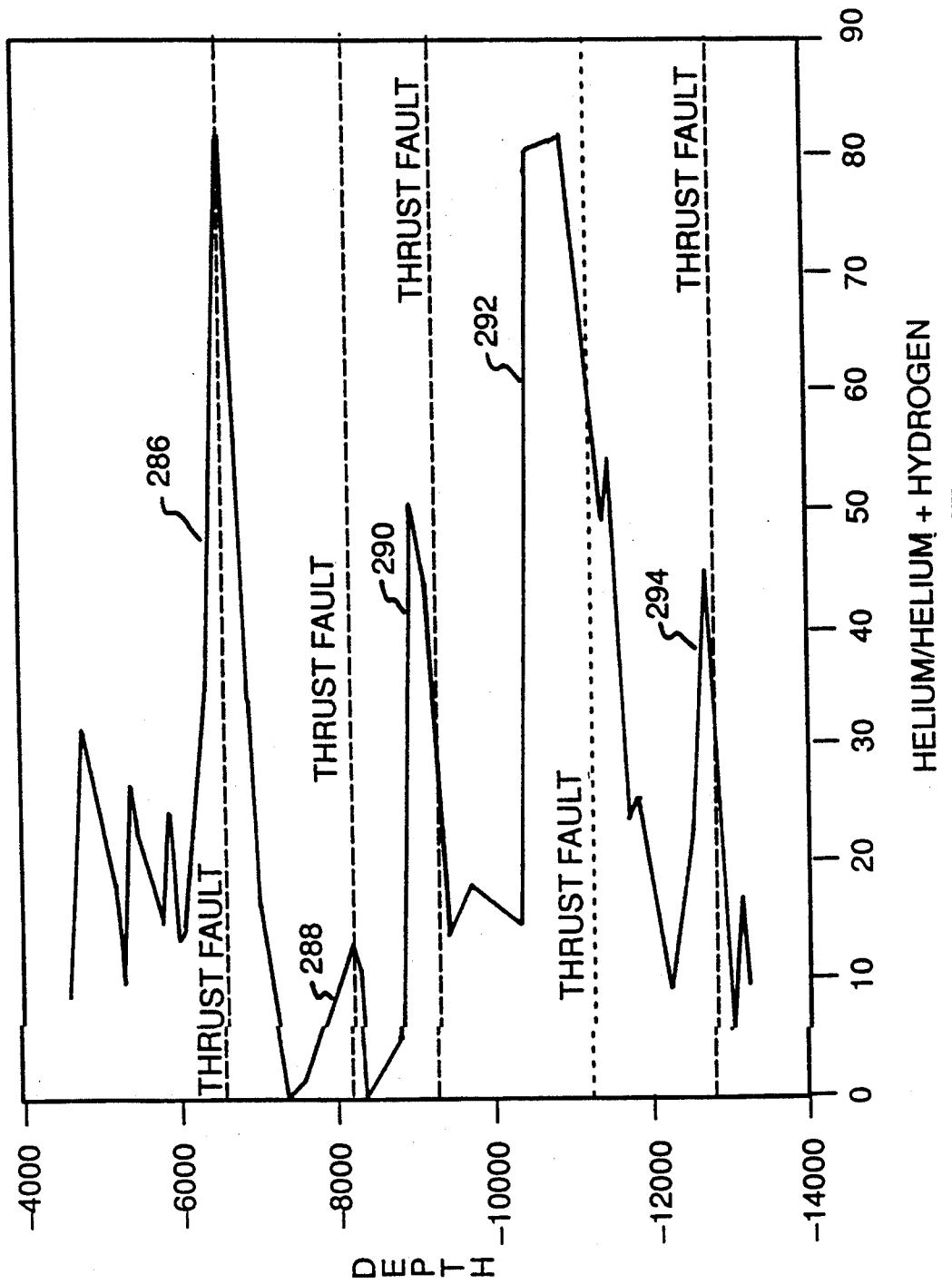

5,286,651

DETERMINING COLLECTIVE FLUID INCLUSION VOLATILES COMPOSITIONS FOR INCLUSION COMPOSITION MAPPING OF EARTH'S SUBSURFACE

This application is a continuation of application Ser. No. 398,341, filed on Aug. 24, 1989, now abandoned.

FIELD OF THE INVENTION

The invention relates to interpreting subsurface structure and history by analysis of fluid inclusions in sedimentary rock samples taken from the subsurface. In one aspect, the invention relates to apparatus and method releasing and/or analyzing volatiles released from myriad fluid inclusions in each of a plurality of sedimentary rock samples. Such volatiles samples released from myriad fluid inclusions in a sedimentary rock sample are referred to herein as collective volatiles or collective fluid inclusion volatiles. In another aspect, the invention relates to methods of oil and gas exploration by chemical region mapping of the subsurface using composition analysis of collective volatiles.

SETTING OF THE INVENTION

The formation and migration of hydrocarbon in sedimentary basins are responsible for the world's petroleum resources. Diagenetic minerals, overgrowths, and veinlets generally contain myriad inclusions smaller than 10 microns of different generations, that is, of different times of development.

Fluid inclusions in minerals are trapped portions of the ambient liquid and gases present during mineral growth or fracture healing and can be used to identify the environment in which formation occurred. Sedimentary rock is characterized by large numbers of fluid inclusions formed at different times and representing different environments. The frequency of occurrence of inclusions per unit weight of sedimentary rock sample varies considerably, but, based on reasonable assumptions, is on the order of $10^3$ to $10^9$ inclusions per cubic centimeter of sedimentary rock. It is this order of magnitude of occurrence of fluid inclusions in sedimentary rocks such as carbonates, sandstones, and shales which is referred to herein as myriad fluid inclusions. Individual rock samples may have fewer inclusions.

The systematic analysis of inclusions could pinpoint areas where particular fluids such as hydrocarbons have been active and other information useful to the oil and gas explorationist. The difficult and time consuming methods presently available inhibit analysis of this fluid record.

In view of the large numbers of inclusions present in a sample, selective individual analysis of individual fluid inclusion data is ineffective for mapping the subsurface, though it can provide valuable information. Succinctly stated, it is too difficult to obtain sufficient data by analysis of individual fluid inclusions for efficient chemical mapping of the subsurface using fluid inclusion data. In addition, virtually any selection technique tends to choose certain inclusions and exclude others. Size and appearance of the inclusions themselves influence selection. Researchers may tend to select larger more well formed inclusions for investigation, yet smaller poorly formed inclusions can contain much valuable information. Since inclusions are being formed continuously, such selection biases results.

Prior art methods for opening more than one fluid inclusion are known, such as by heating, e.g., by furnace or laser, or by crushing. Heating, however, is not effective for opening many gaseous inclusions since there are too few moles of gas present in the inclusion to develop sufficient pressure under usual heating conditions.

Crushing techniques for releasing contents of myriad inclusions have been such as placing rock samples in a metal sample tube, crimping the tube's ends, and crushing the tube using hammers or the like. Analysis then involves opening the sample tube in a controlled environment releasing and capturing the volatiles, and analyzing for water, $CO_2$, $N_2$, and hydrocarbon content. Such technique is tedious and time consuming and not suitable for processing large numbers of samples and moreover, omits to obtain composition data of great importance as will be apparent from the description of this invention.

Moreover, the described crushing technique results in biased results. The technique is not effective for observing $H_2S$ since $H_2S$ can react with the metal. Further, the long residence time of the released gases with the surfaces freshly exposed by crushing can result in adsorption changing the apparent composition of inclusion volatiles. A technique is needed in which volatiles are instantaneously removed from the sample and analyzed as they are being released without contact with materials which can significantly alter composition of released volatiles.

The invention relates to method and apparatus for determining composition of collective fluid inclusion volatiles of large numbers of samples of subterranean sedimentary rocks simply, rapidly, and without need for extensive sample preparation and handling compared to prior art methods.

The invention also relates to method and apparatus for analysis of collective fluid inclusion volatiles which provide an adequate record, suitable for analysis, of most all of the elements and compounds which are found in fluid inclusions.

The invention also relates to stratigraphic and/or inclusion composition mapping of the subsurface, and oil and gas exploration using the results of such analyses.

SUMMARY OF THE INVENTION

The invention relates broadly to a method for analyzing fluid inclusions in sedimentary rock. A plurality of sedimentary rock samples are placed in a plurality of sample chambers. The plurality of sample chambers containing rock samples are placed in an evacuable chamber. The chamber is evacuated. A rock sample in a sample chamber is impacted effective for releasing a collective volatiles sample from myriad fluid inclusions in the rock sample. The collective volatiles sample is removed from the chamber and its composition is analyzed. A further rock sample is impacted to release a collective volatiles sample. The preceding two steps are repeated until the plurality of rock samples in respective rock chambers have individually been crushed in sequence and volatiles released and composition analyzed. Then, the vacuum on the evacuable chamber is released and the plurality of sample chambers are removed.

According to an aspect of the invention, the earth's subsurface is stratigraphically and interpretively mapped using composition data from statistically and stratigraphically significant numbers of collective fluid inclusion volatile samples from different locations relative to the earth's surface and/or from different depths in the earth.

According to another aspect of the invention, apparatus is provided for sequentially releasing a respective collective fluid inclusion volatile sample from each of a plurality of sedimentary rock samples and for delivering the resulting plurality of collective volatile samples to analysis means for determining composition of each sample.

The release of collective fluid inclusion volatile samples sequentially from each of a plurality of sedimentary rock samples occurs in an evacuated chamber which is adapted to receive, support and maintain separate each of a plurality of rock samples during release of collective fluid inclusion volatiles. Means inside the chamber individually impact in a timed sequence each rock sample effective for releasing a collective volatiles sample therefrom without generally releasing the vacuum on the chamber. During times of impacting successive samples, each collective volatile sample is provided continuously to analysis means for determining composition.

According to an aspect of the invention, the composition of released fluid inclusion volatiles is determined using method and apparatus effective for mass spectroscopic (MS) analysis of collective fluid inclusion volatiles. According to this aspect, a series of rock samples can be quickly and rapidly analyzed to produce mass spectra of mass to charge ratio (m/e or MCR) responses across a range of such values encompassing abundant and trace inorganic and organic elements and compounds in inclusions which are useful in interpreting the earth's history. Thus, stratigraphically and statistically large data sets become available which are suitable for stratigraphic mapping of subsurface structure.

According to a further aspect of the invention, the earth's subsurface is stratigraphically mapped using zones each having characteristic composition data over a plurality of collective fluid inclusion volatile samples from a plurality of locations in the earth. The composition data are obtained indiscriminately from all or substantially all of the hydrocarbon, aqueous, gaseous, and mixed fluid inclusions present in rock samples. The resulting data represent oxygen, nitrogen, argon, neon, xenon, carbon dioxide, ammonia, sulfate, hydrogen chloride, hydrogen sulfide, methane and other light hydrocarbons, heavier hydrocarbons such as paraffins and naphthenes, water-soluble hydrocarbons, as well as other compounds occurring in analyzable quantities in aggregated released fluid inclusion volatiles.

DESCRIPTION OF THE INVENTION

The invention will be further understood and appreciated from the following FIGURES which are described here briefly and below in detail.

Figure 5A:
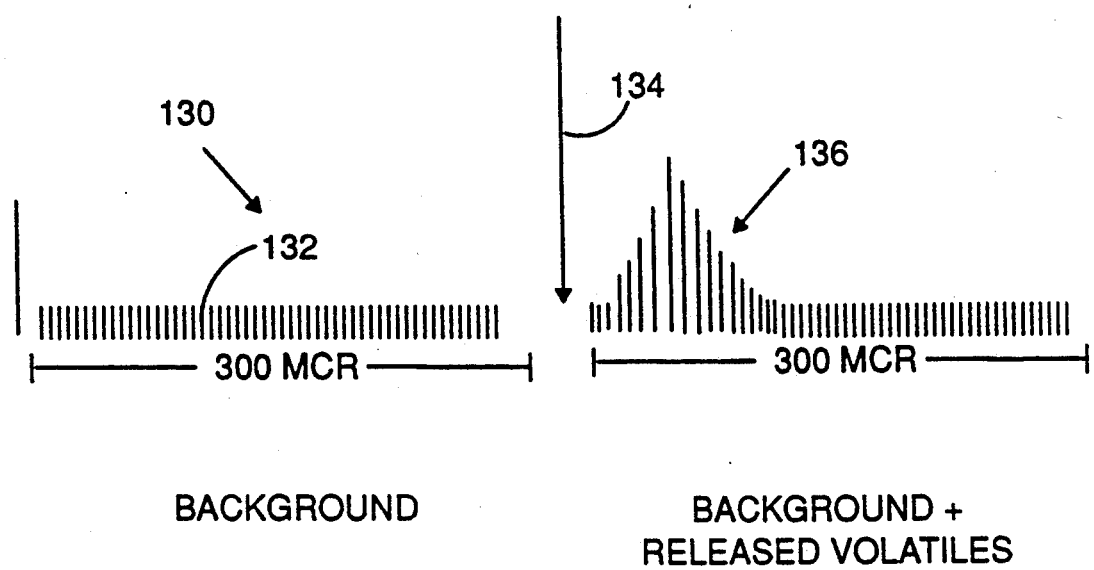

FIG. 5A schematically illustrates measurement of autosampler background data and of autosampler background data plus collective fluid inclusion sample data.

Figure 5B:
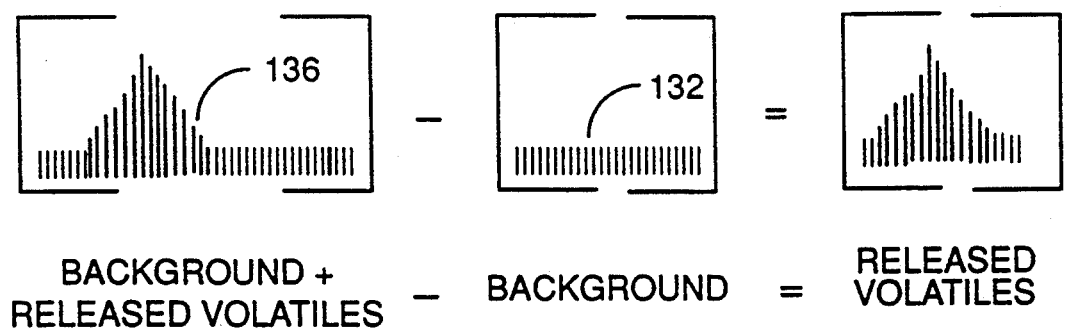

FIG. 5B illustrates distinguishing inclusion from non-inclusion gases by subtracting background data from sample data.

Figure 6A:
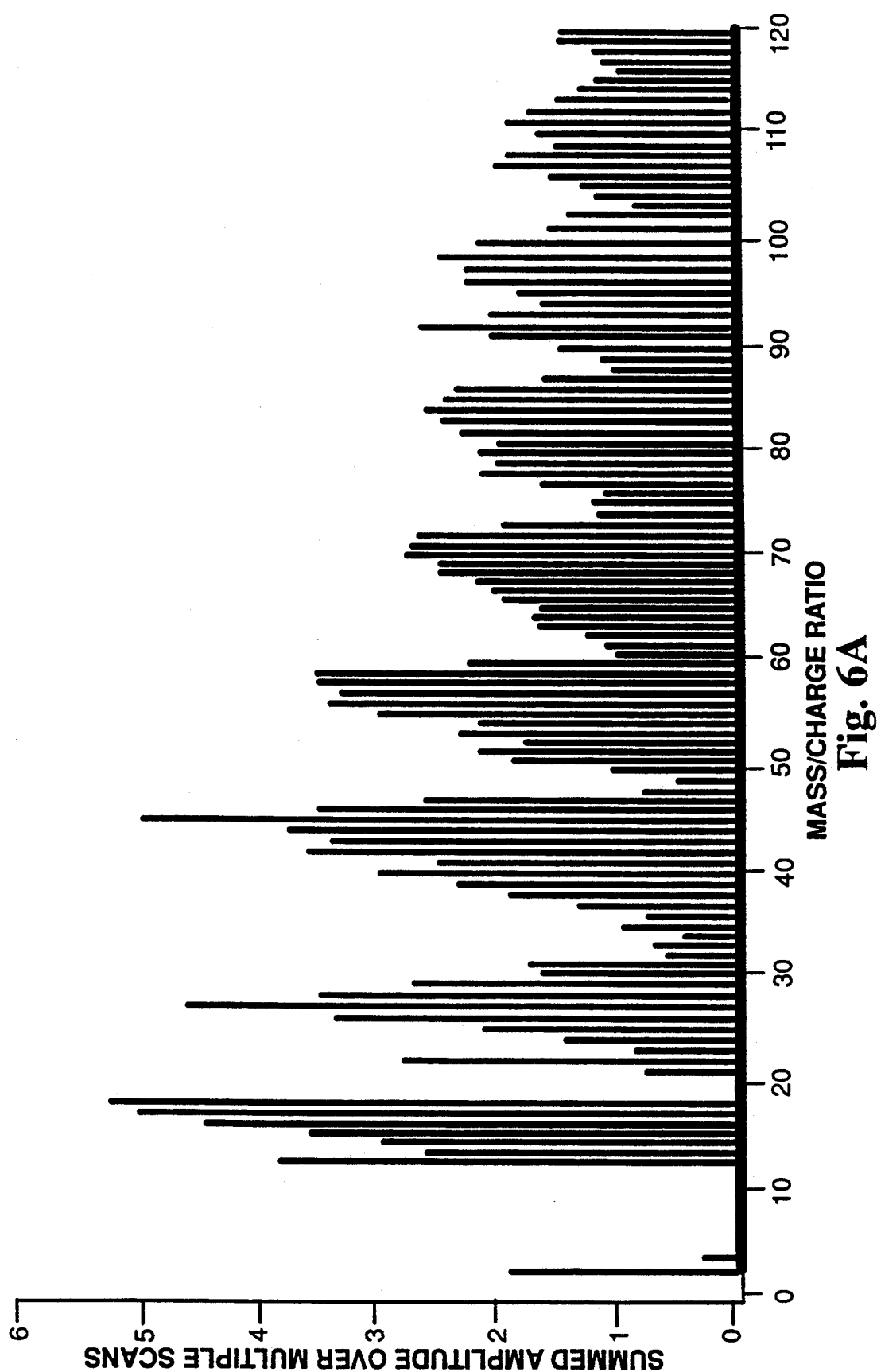

FIG. 6A illustrates a logarithmic scale MCR spectrogram of a collective fluid inclusion volatiles sample.

Figure 6B:
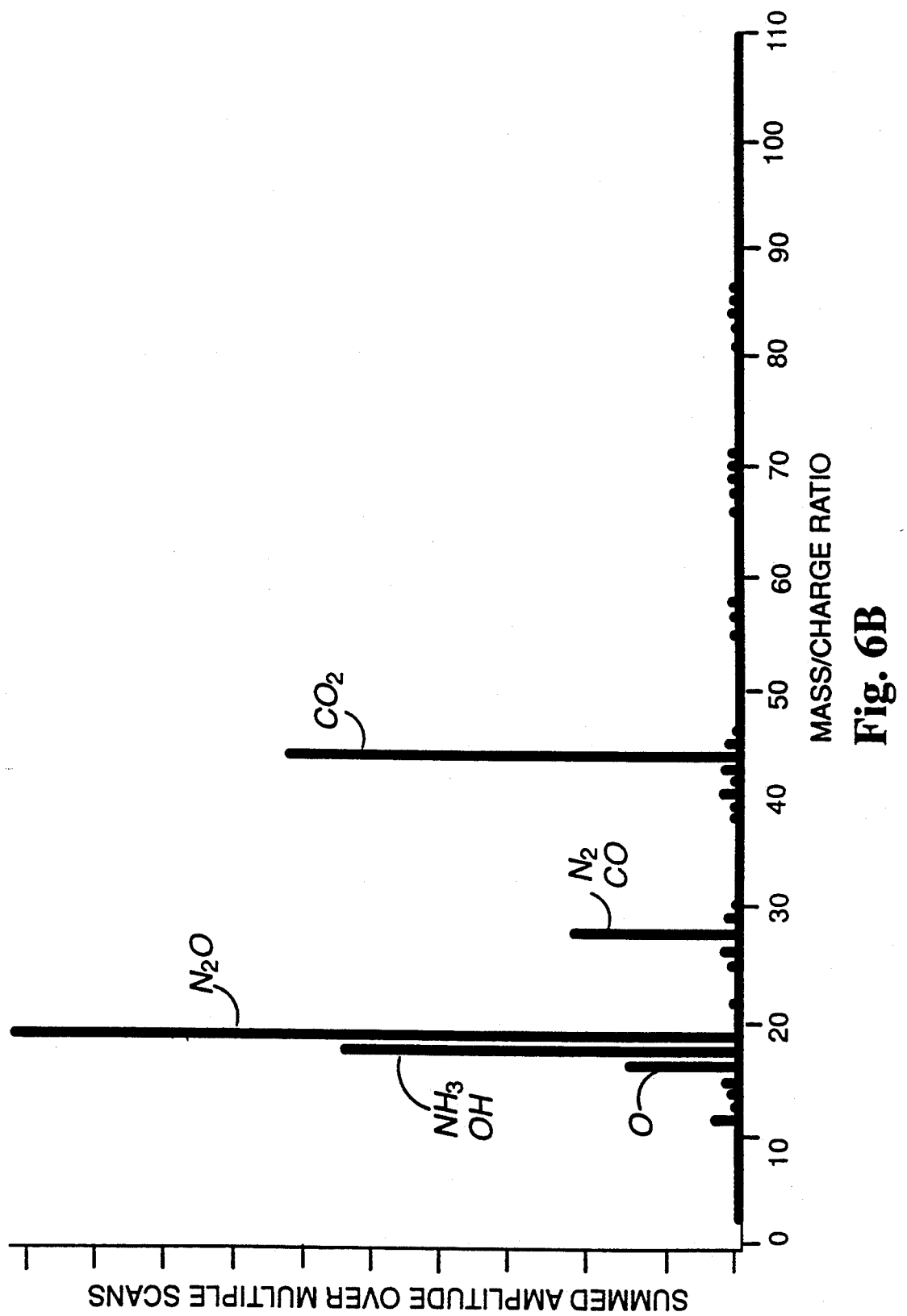

FIG. 6B illustrates a linear scale MCR spectrogram of FIG. 6A.

FIG. 7 illustrates a ternary plot of fluid inclusion composition data showing two zones having characteristic fluid inclusion compositions, each zone representing a plurality of locations in the subsurface.

Figure 8:
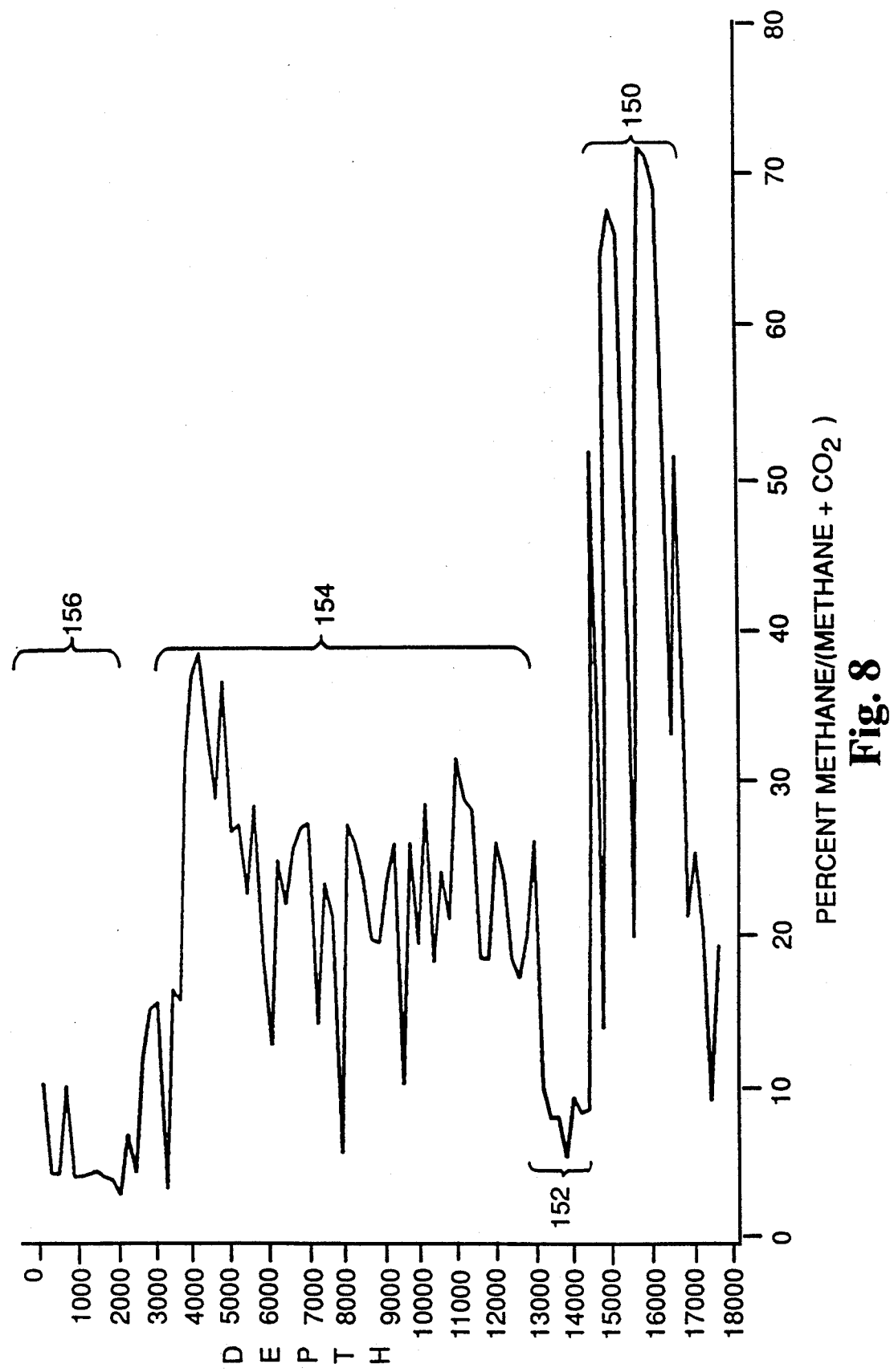

FIG. 8 illustrates a log displaying as a function of depth variations in abundance of methane in collective fluid inclusion volatiles in a specific well and illustrates identifying hydrocarbon migration zones and seals.

Figure 9:
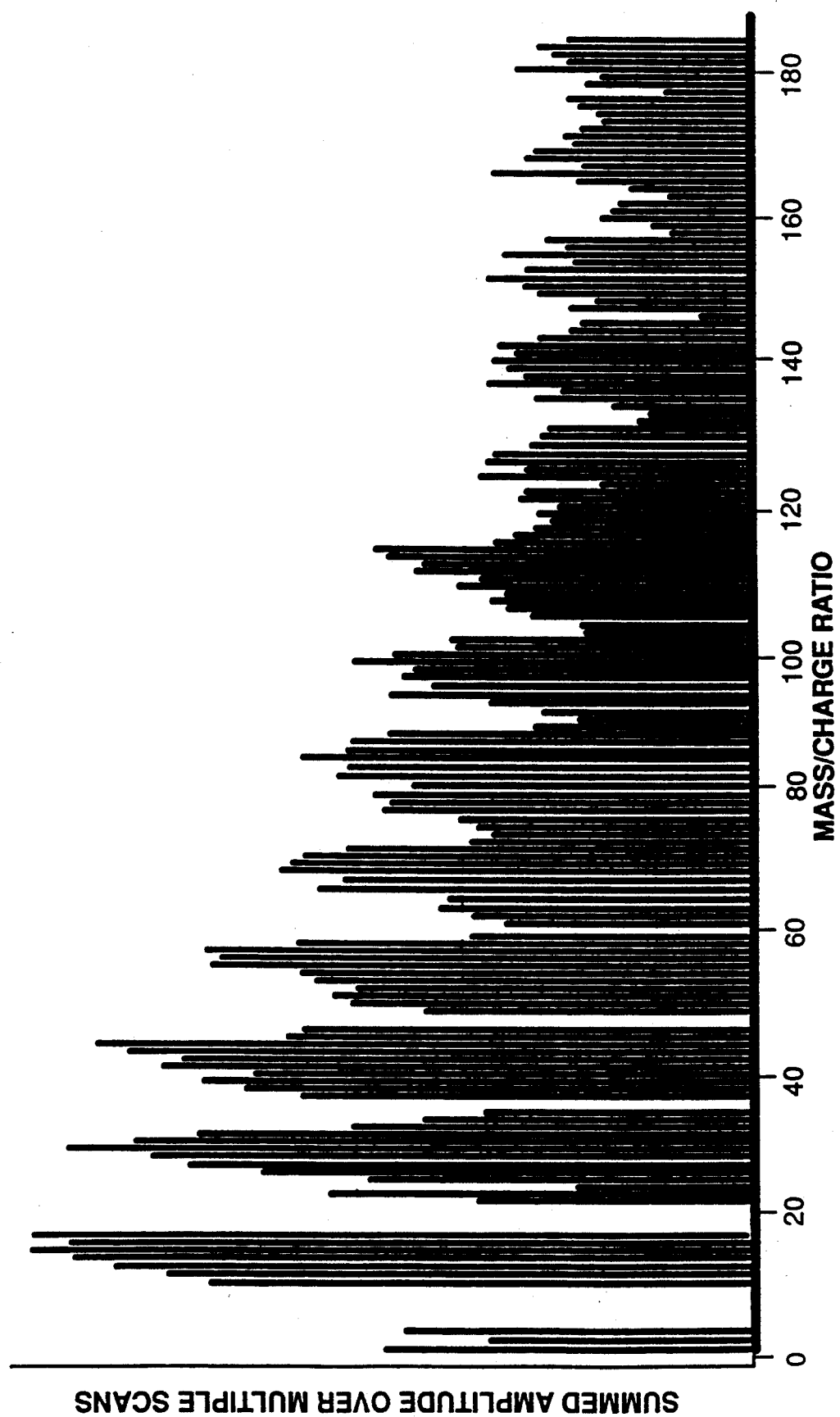

FIG. 9 illustrates a logarithmic MCR spectro-gram of a collective fluid inclusion volatiles sample in zone 150 of FIG. 8.

Figure 10:
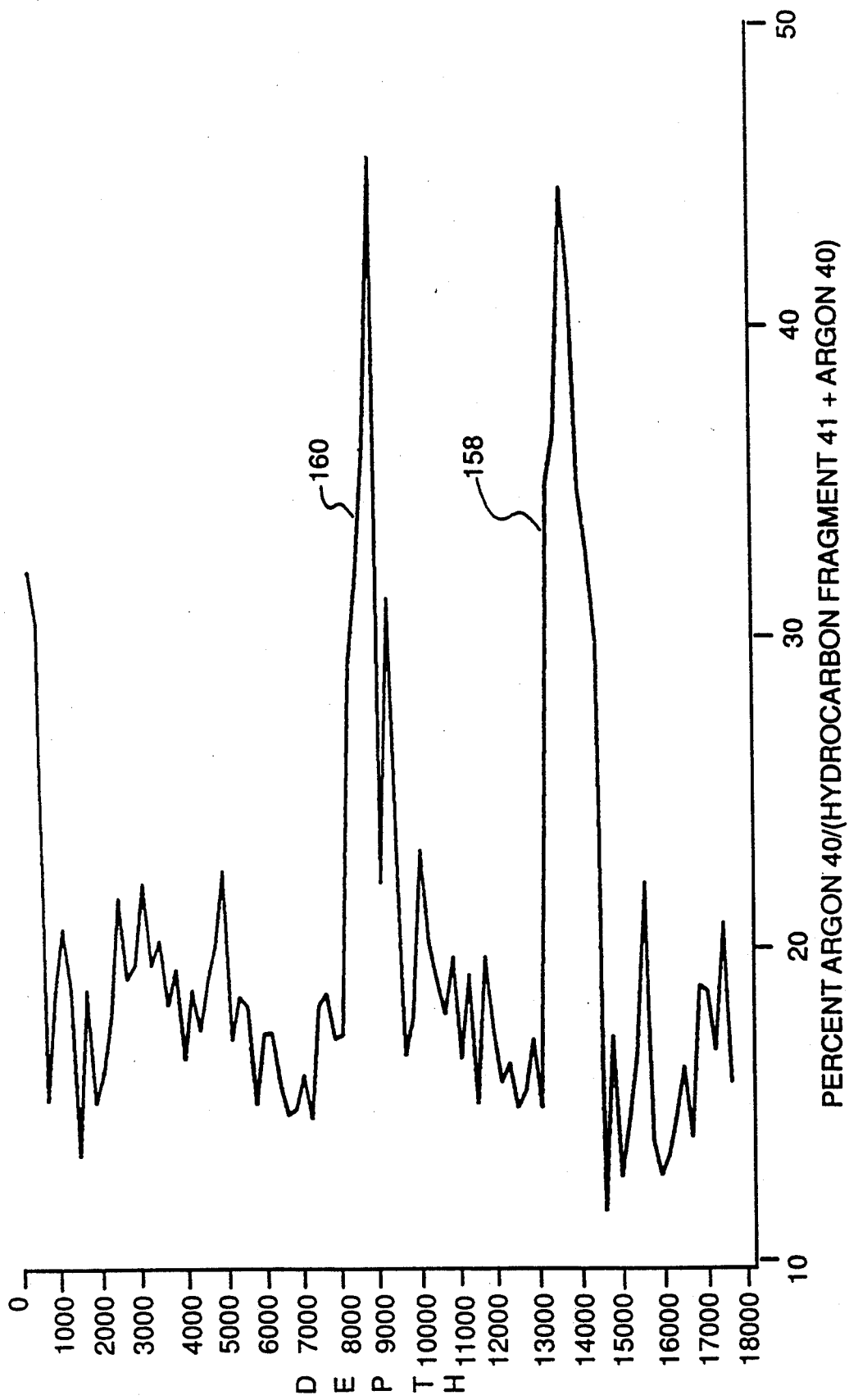

FIG. 10 illustrates a fluid inclusion composition log displaying as a function of depth variations in abundance of argon in a specific well and illustrates identifying paleo-exposure zones.

Figure 11:
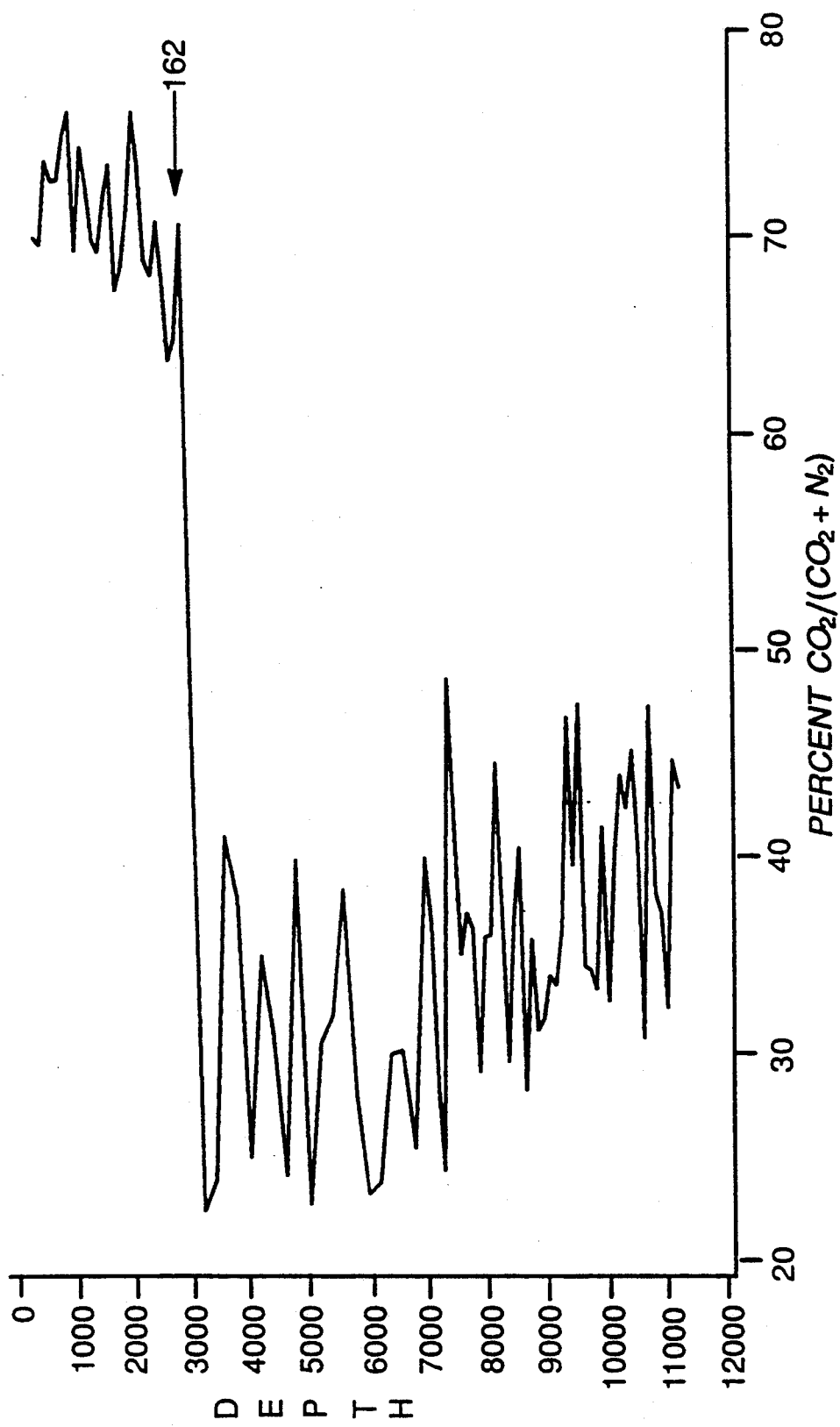
Figure 12:
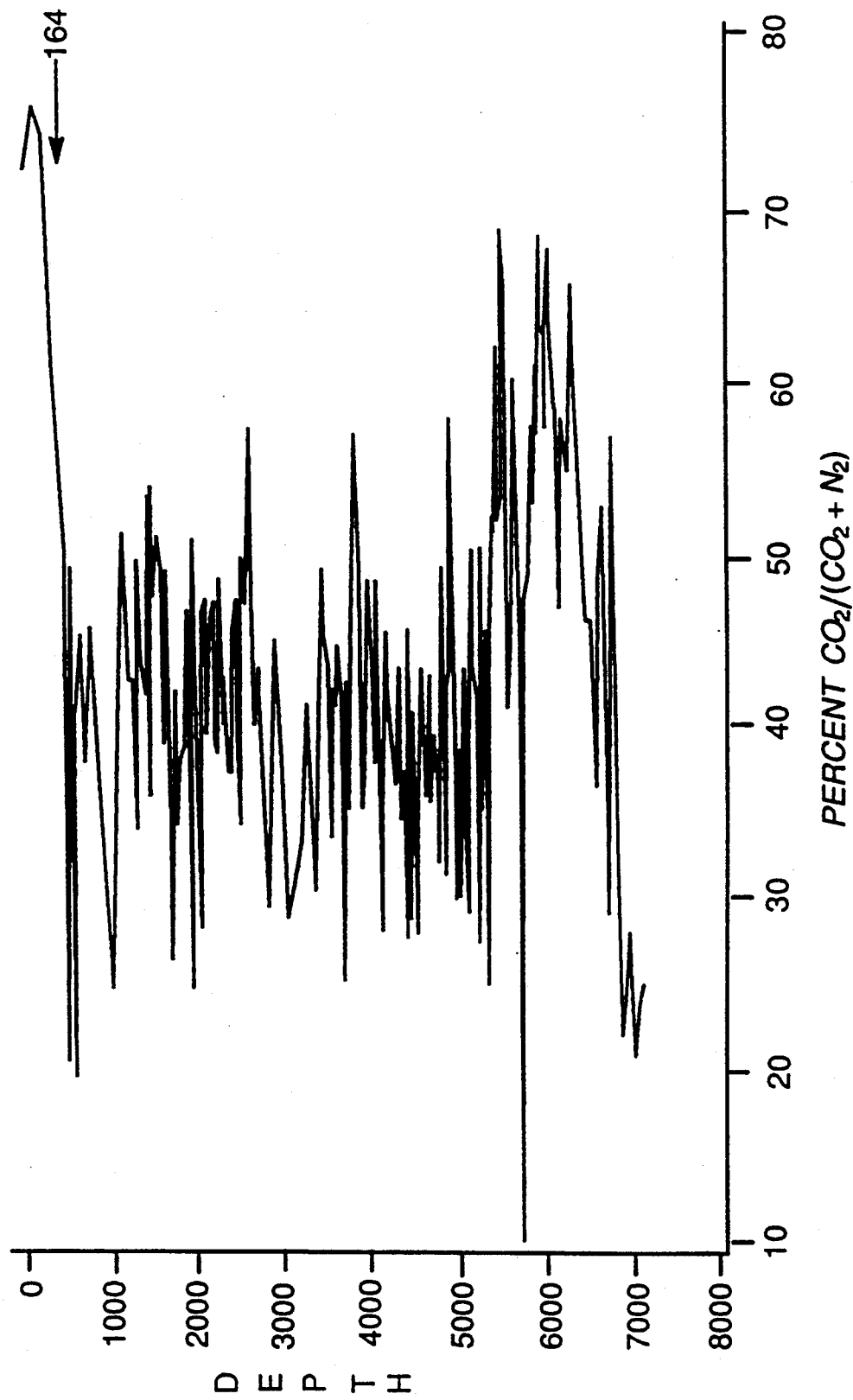

FIGS. 11 and 12 illustrate fluid inclusion composition logs displaying as a function of depth variations in $CO_2$ and illustrate at 162 and 164 respectively a fluid inclusion composition region in the subsurface having wide applicability as a stratigraphic time marker.

Figure 13:
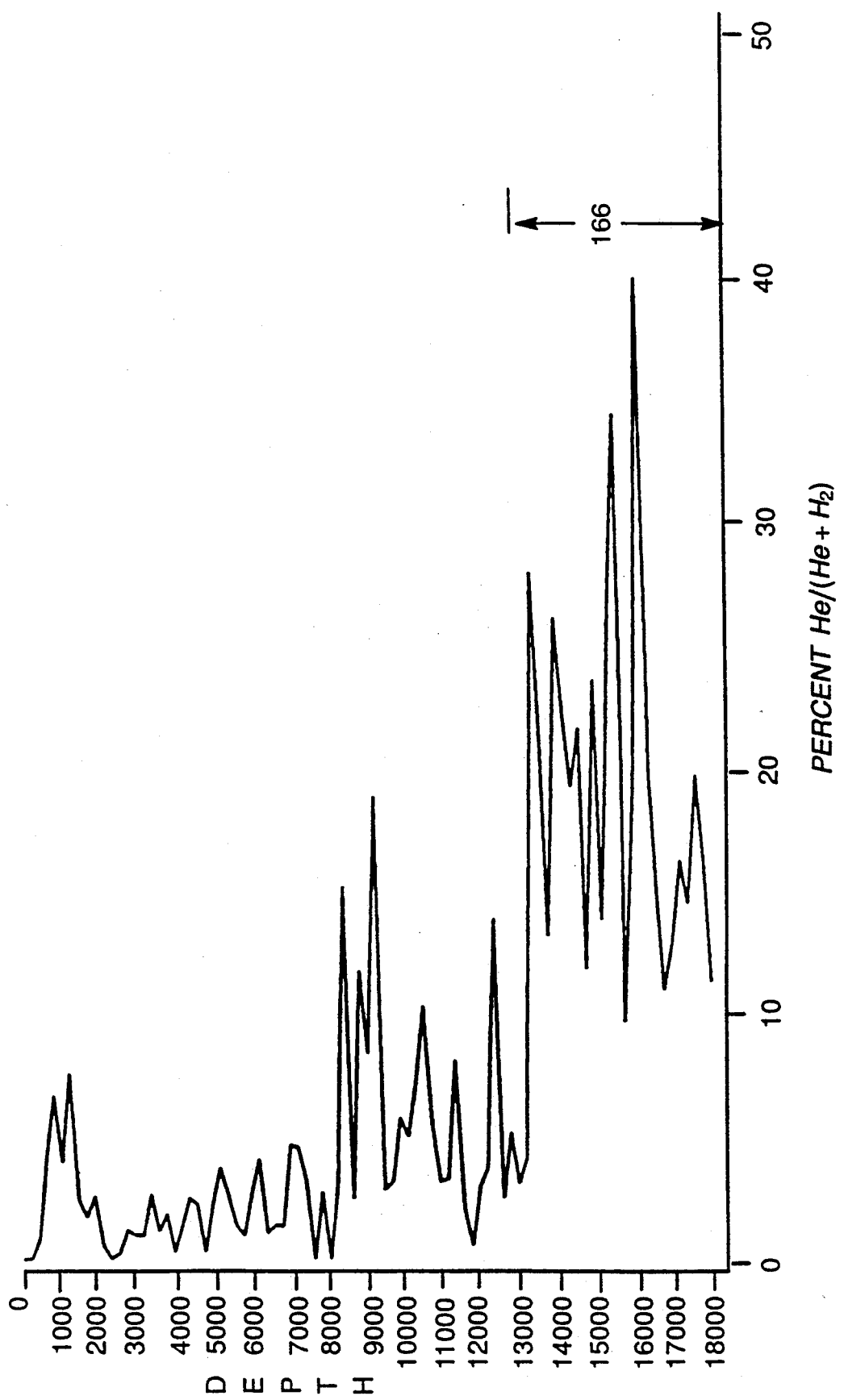

FIG. 13 illustrates a fluid inclusion composition log displaying as a function of depth variations in helium and illustrates another fluid inclusion composition region in the subsurface having wide applicability as a stratigraphic time marker.

Figure 14A:
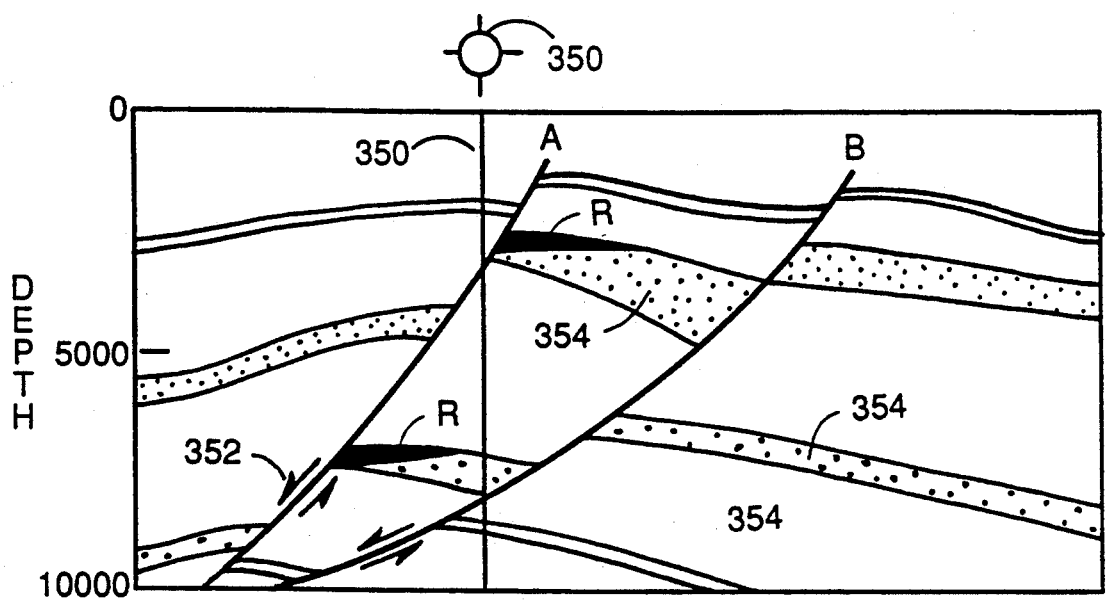

FIG. 14A represents a well testing a simple fault trap.

Figure 14B:
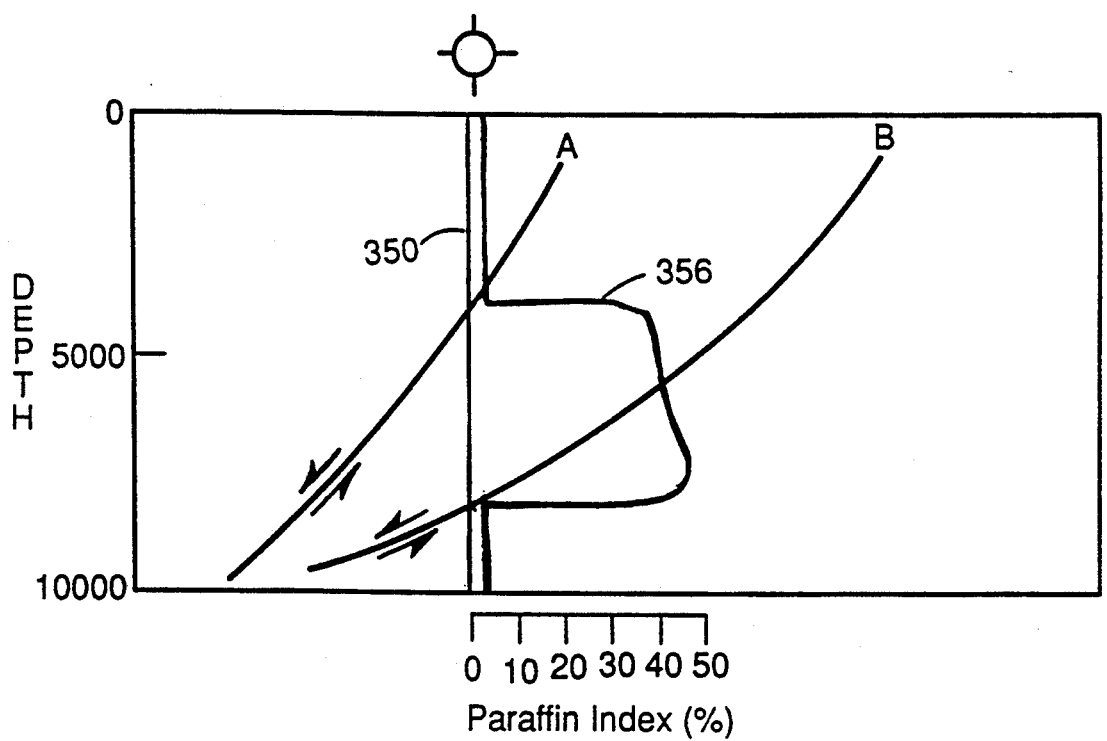

FIG. 14B represents a log display showing a fluid inclusion composition region as a function of depth characterized by paraffin abundance superimposed on the well of FIG. 14A.

Figure 15A:
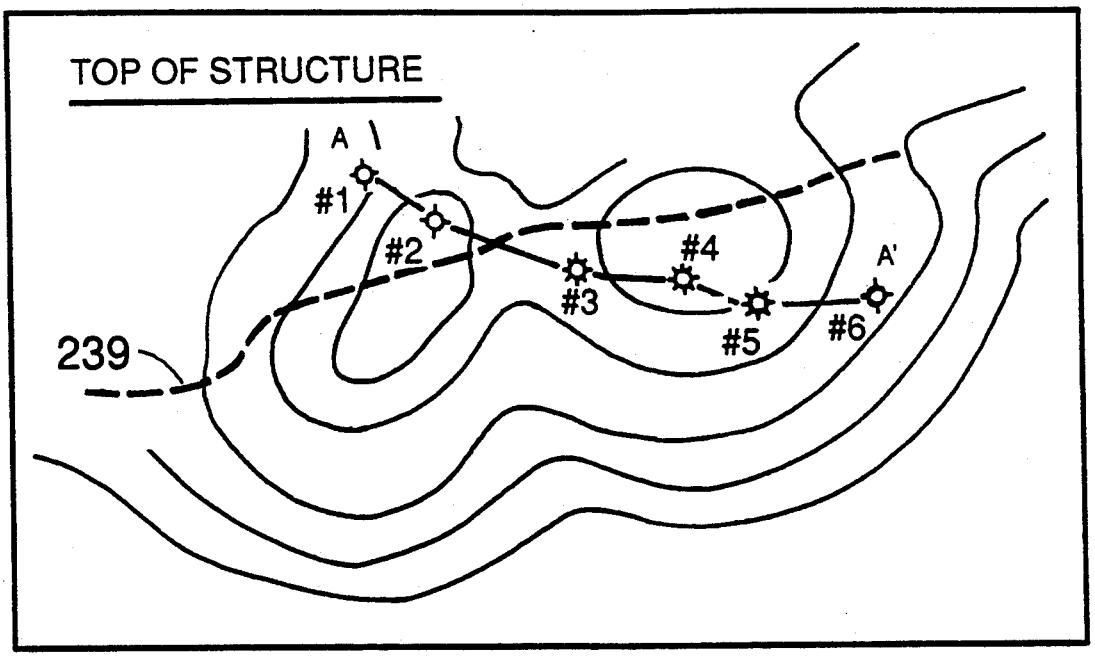

FIG. 15A illustrates a structural contour map of a producing formation.

Figure 15B:
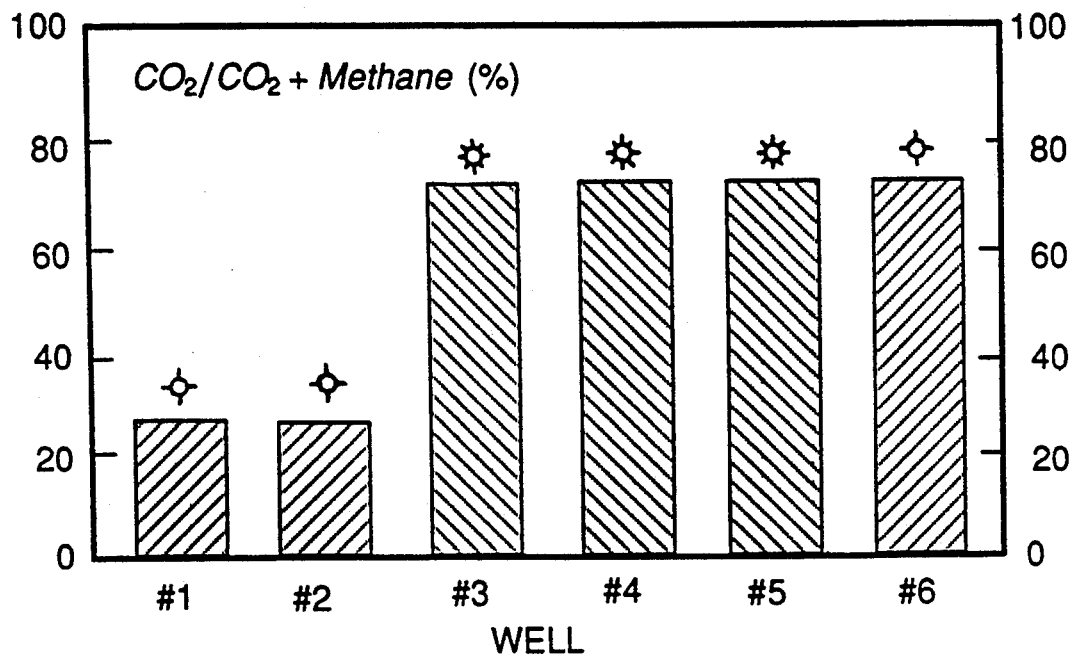

FIG. 15B illustrates variations in $CO_2/(CO_2+\text{methane})$ in inclusions adjacent wells in FIG. 15A.

Figure 15C:
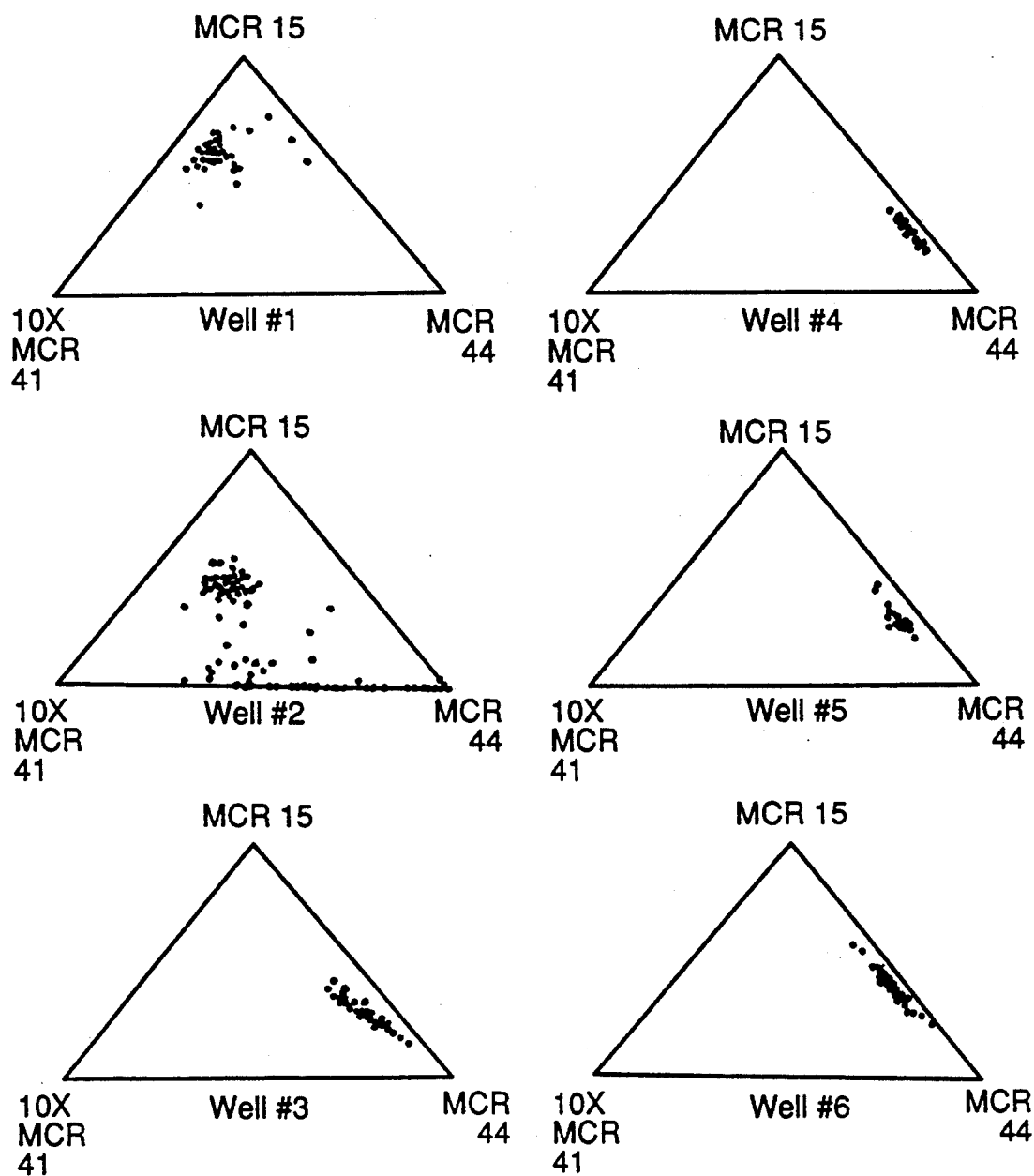

FIG. 15C illustrates ternary diagrams for wells in FIG. 15A showing relative variation in methane, $CO_2$, and MCR41 representing heavier hydrocarbons.

Figure 15D:
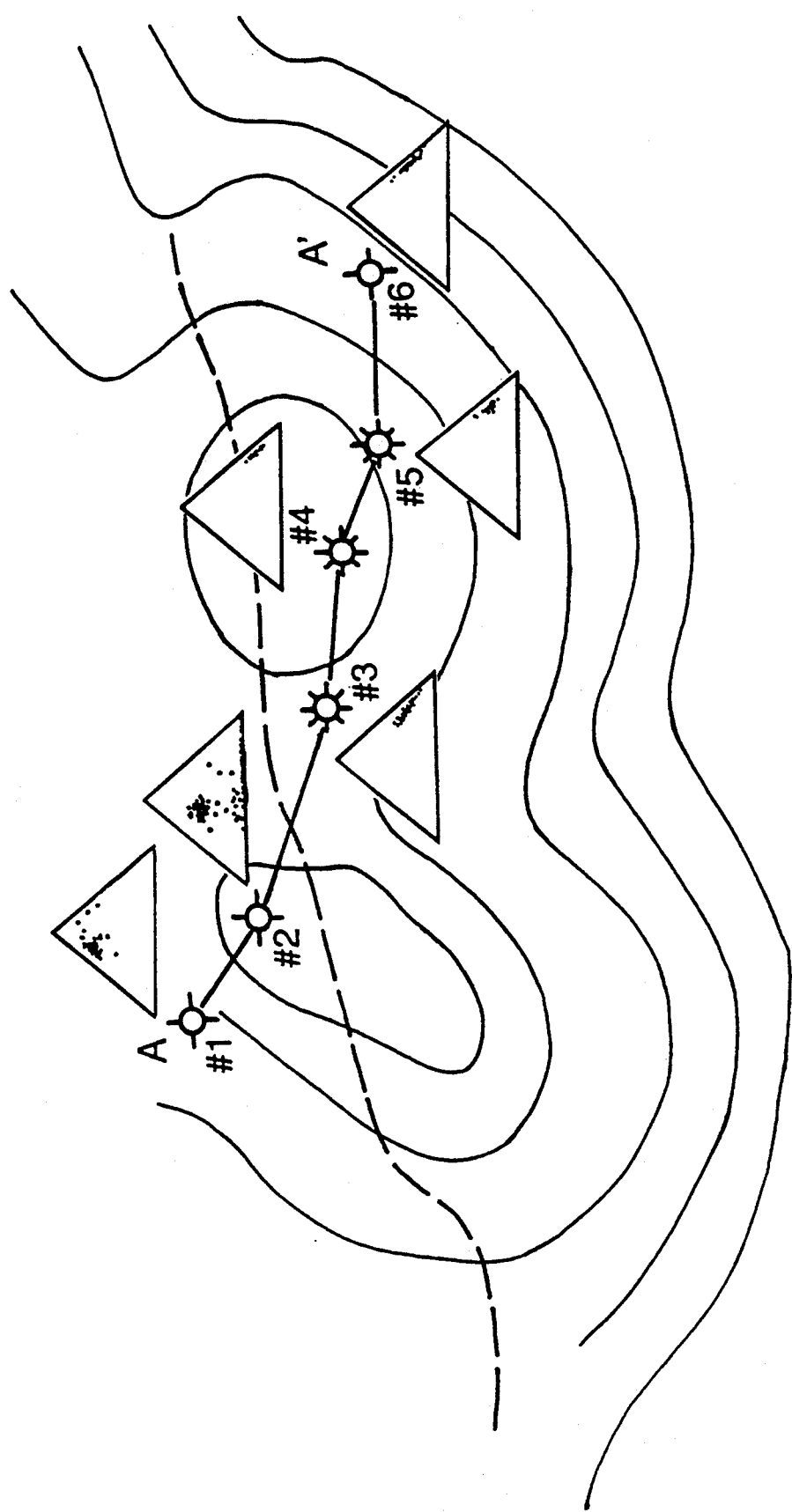

FIG. 15D illustrates variations in collective fluid inclusion volatiles compositions by displaying ternary plots of FIG. 15C on a map (FIG. 15A) of a subterranean structure.

Figure 16A:
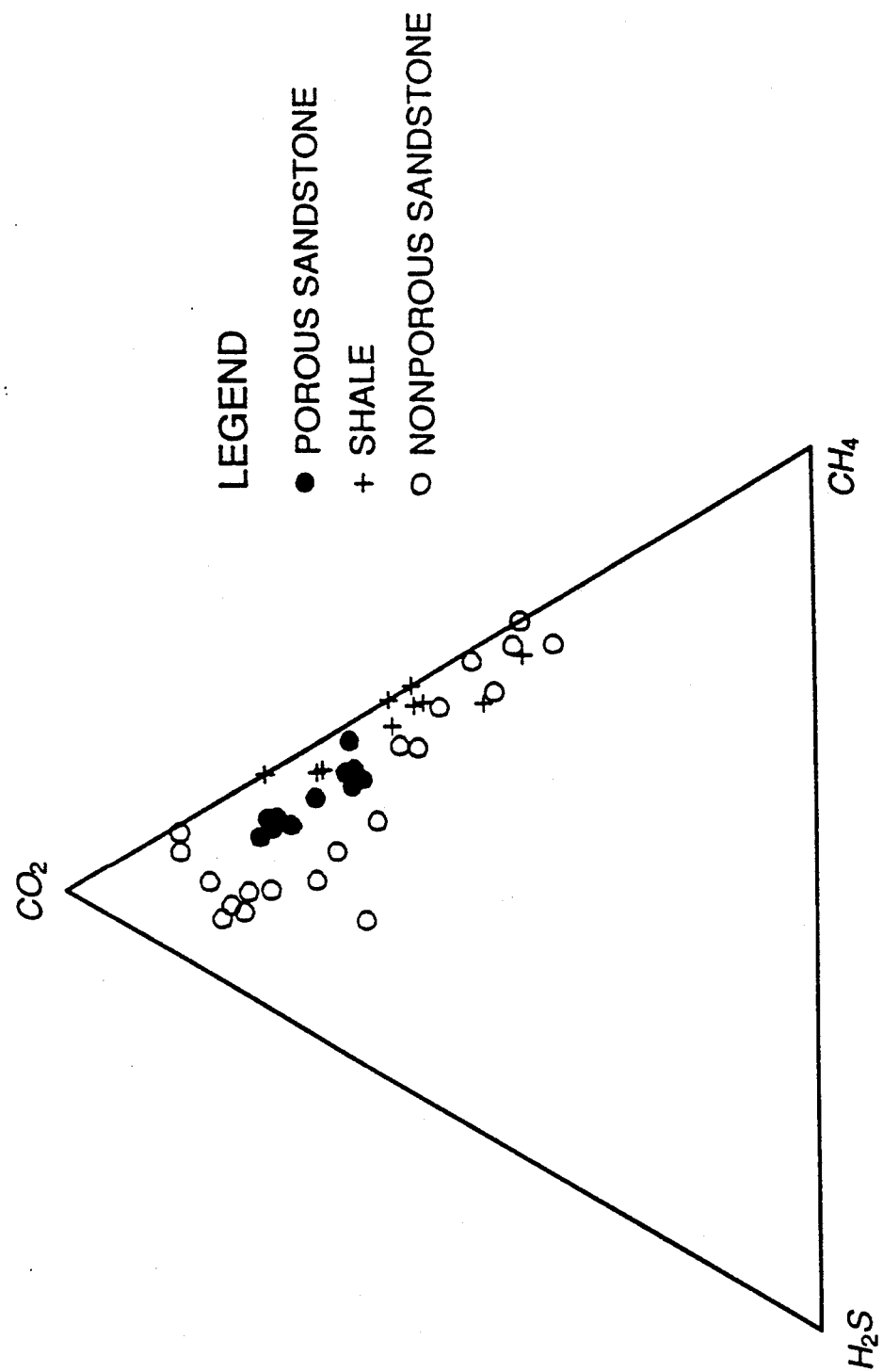

FIG. 16A illustrates a ternary plot in accordance with the invention of $CO_2/CH_4/H_2S$ variation in fluid inclusions volatiles in formations adjacent a well.

Figure 16B:
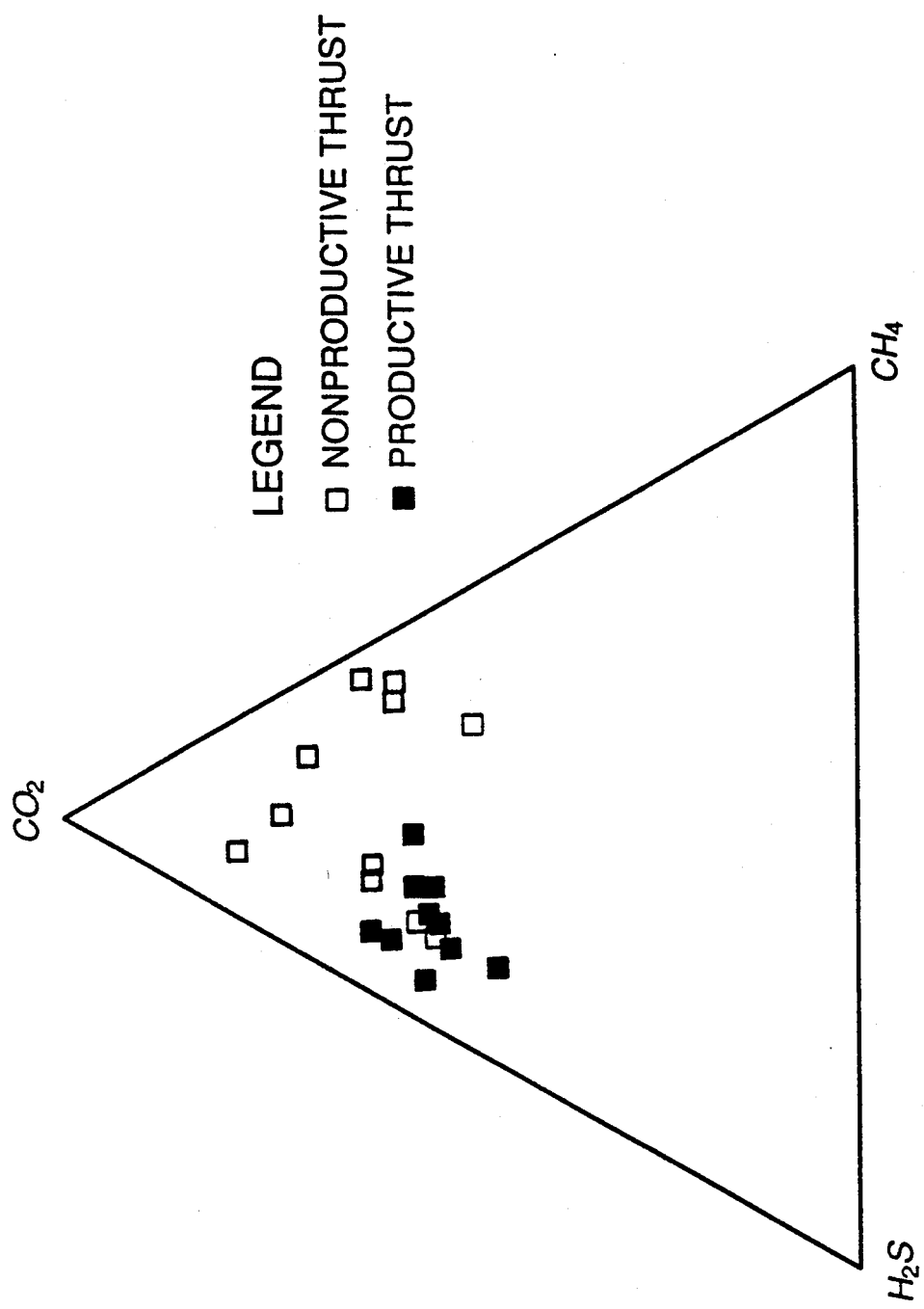

FIG. 16B illustrates a ternary plot in accordance with the inventions showing different characteristic populations of $CO_2/CH_4H_2S$ inclusion volatiles compositions of productive and nonproductive thrusts.

Figure 16C:
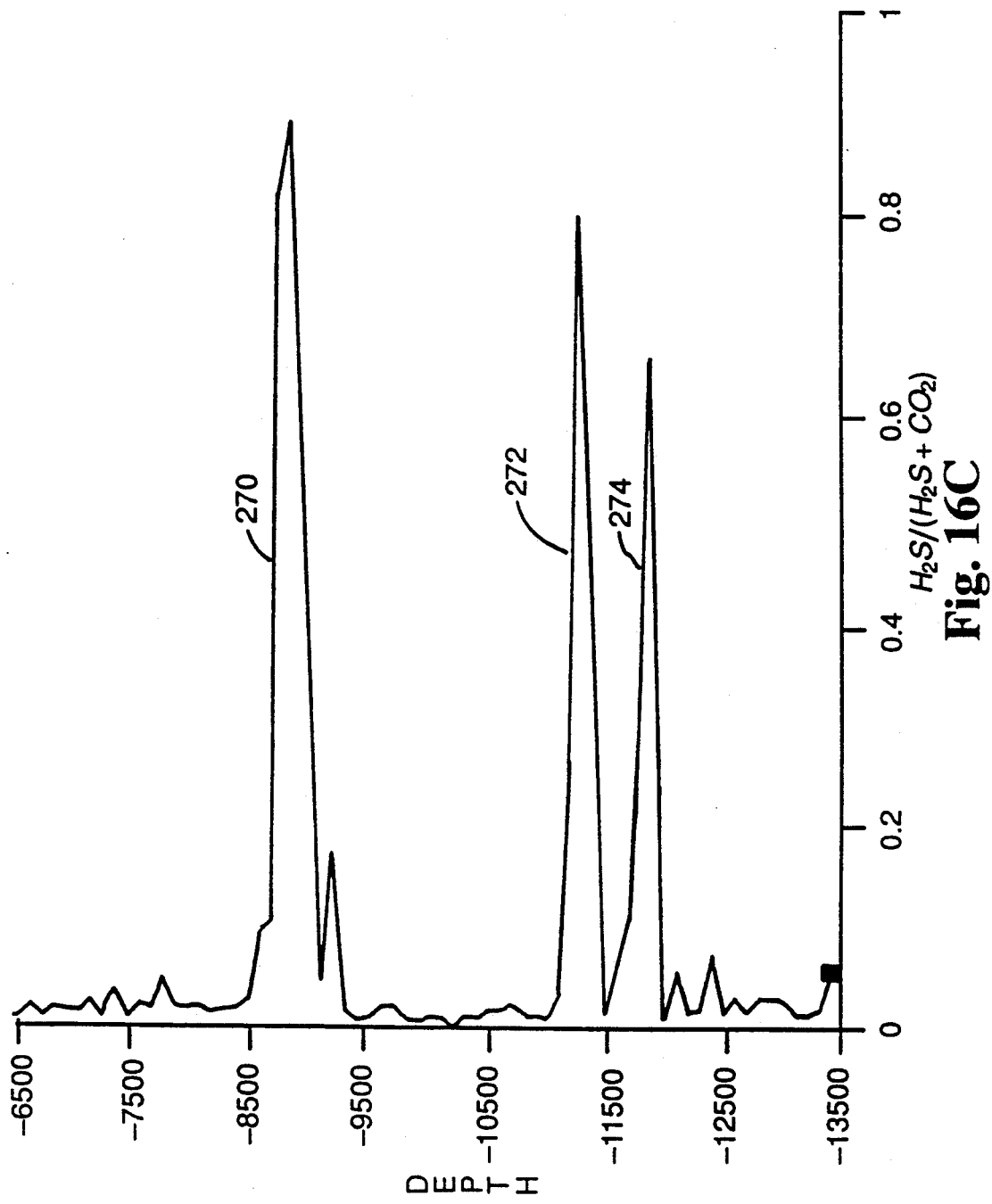

FIG. 16C illustrates a log display of $H_2S$ normalized relative to $CO_2$ as a function of depth along a borehole.

Figure 16D:
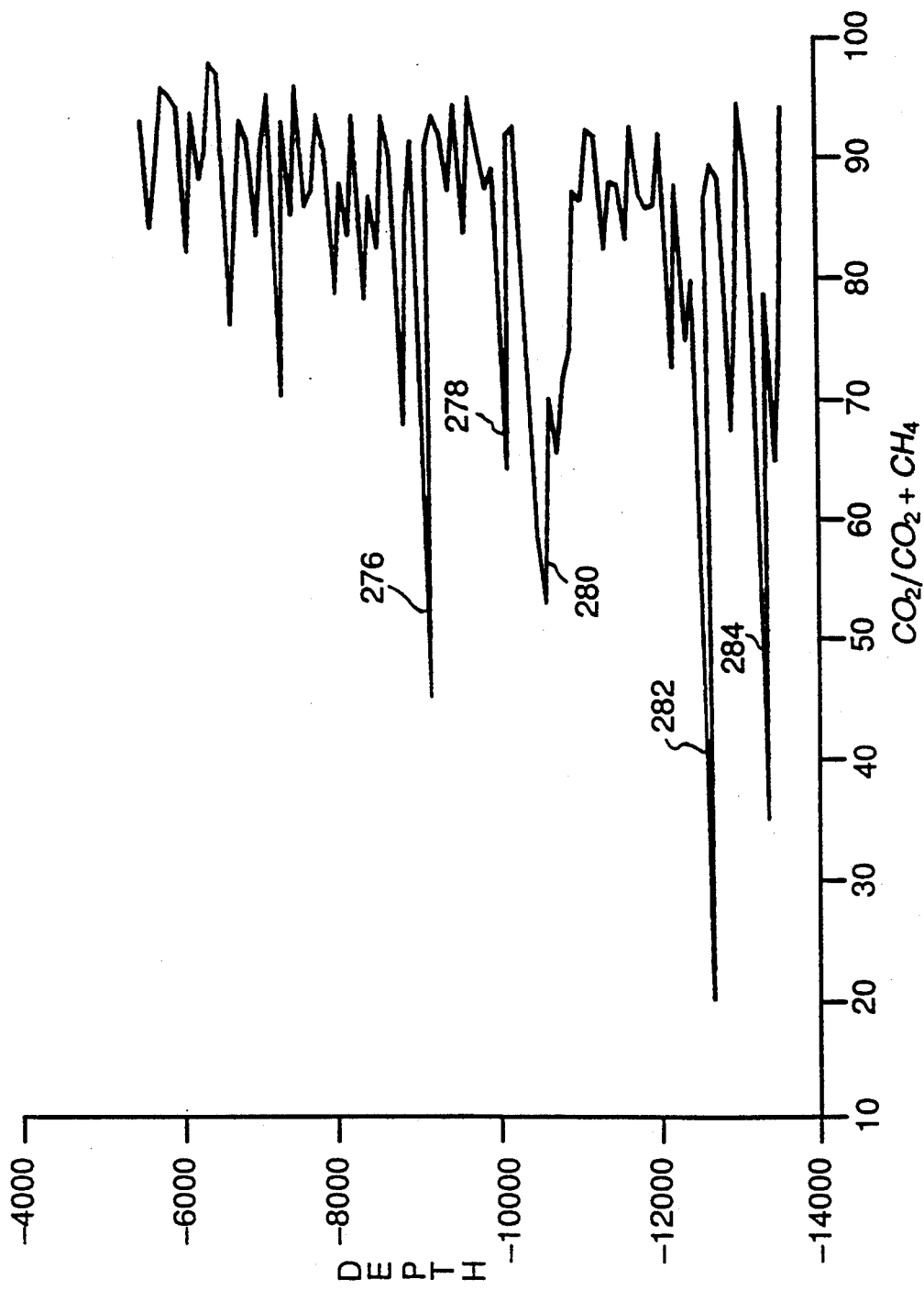

FIG. 16D illustrates a log display of $CO_2$ variation normalized relative to $CH_4$ as a function of depth along a borehole.

FIG. 16E illustrates a log display of helium variations normalized relative to hydrogen as a function of depth along a borehole.

DETAILED DESCRIPTION OF THE INVENTION

Fluid inclusions are trapped fluids occluded in the matrix of the rocks in tiny cavities which do not contribute to the rock's pore system, either to macroporosity or microporosity. Fluid inclusions are classified as hydrocarbon inclusions when liquid hydrocarbons are predominant, aqueous inclusions when liquid water is predominant, and gaseous when gases are predominant. Inclusions can also be classified as liquid-filled or gas-filled. Mixed liquid-and-gas-filled inclusions are also commonly encountered.

The volatile components are released from fluid inclusions and aggregated, for example, by summing during analysis data from large numbers of fluid inclusions in each sedimentary rock sample. The volatiles released are a heterogeneous mixture of released from all the various generations and all the various types of inclusions in each rock sample. Molecules having different molecular weights move through the analysis system at different rates and require an analysis procedure which accurately and precisely reflects the original composition of the mixture. Different samples have different heterogeneous mixtures of fluid inclusions depending on their respective geological histories. By analyzing composition of different heterogeneous samples in a manner effective for obtaining a record of all of the molecules present, variations in composition can be identified which are indicative of differences in populations of fluid inclusions from region to region in the earth.

Figure 1:
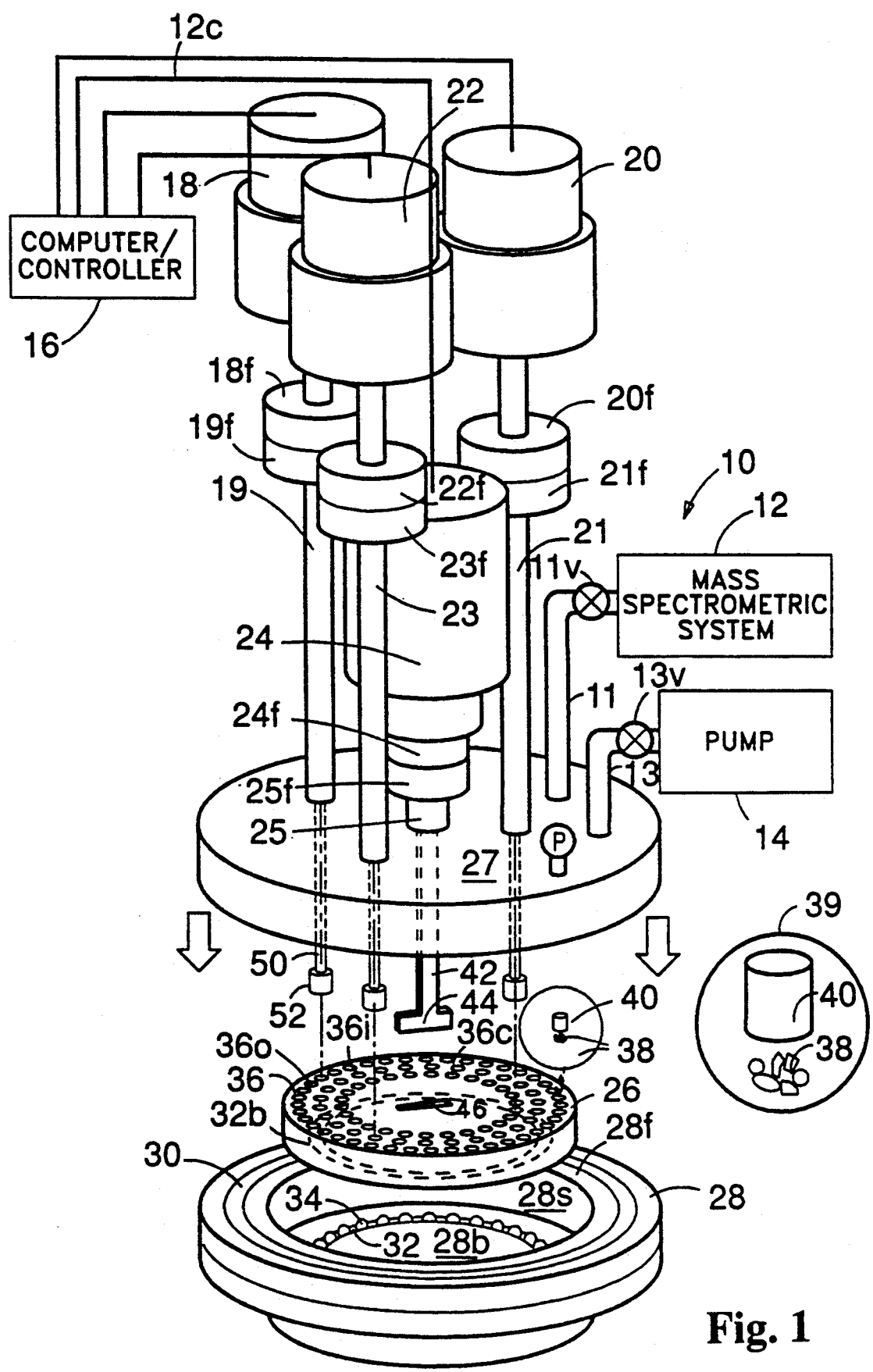
FIG. 1 illustrates, in exploded view, an auto-sampler system for automated production of collective fluid inclusion volatiles samples from each of a plurality of sedimentary rock samples.
Figure 1A:
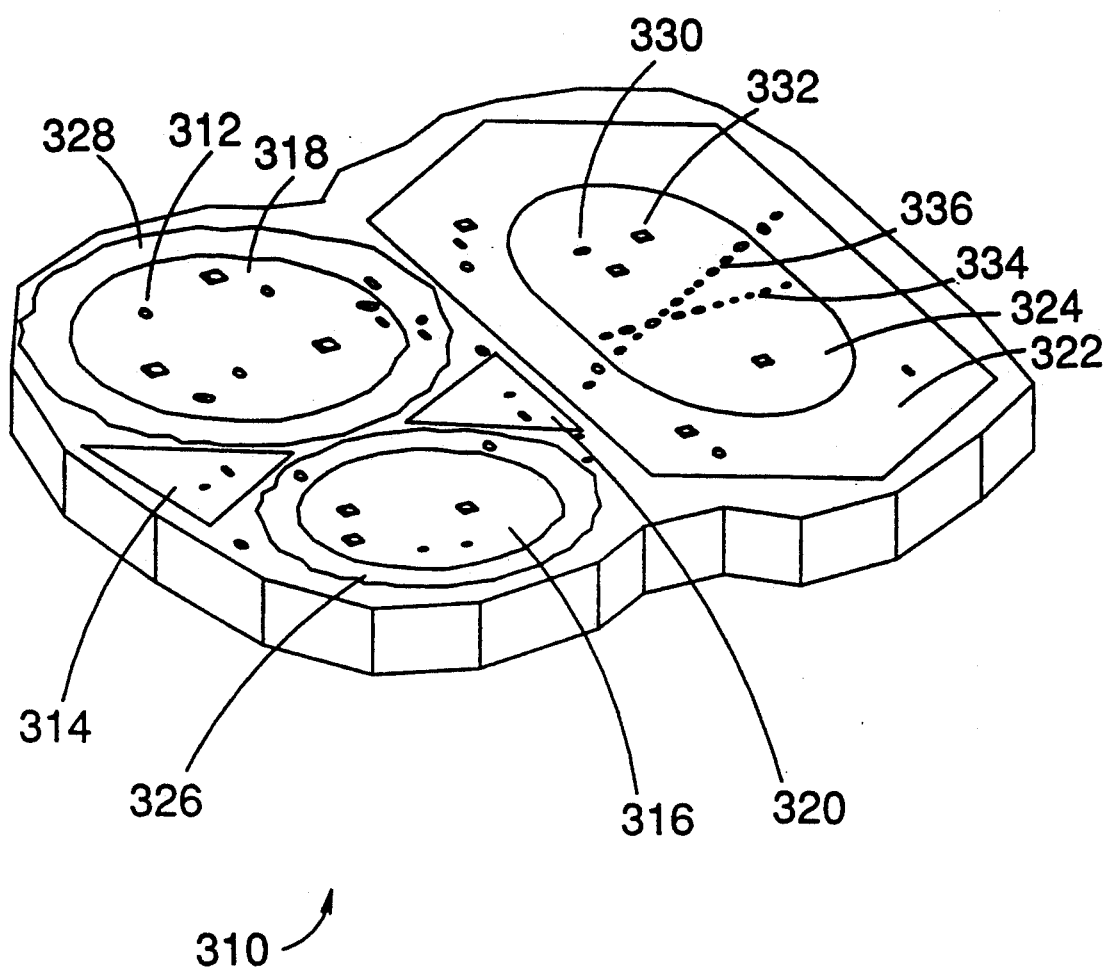
FIG. 1A illustrates occurrence of inclusions in a mineral thin section such as might be taken from rock sample 38 in FIG. 1.

Referring now to FIG. 1A, FIG. 1A illustrates inclusions such as might be observed in a mineral thin section taken from rock sample 38 in FIG. 1.

Indicated generally at 310 is a portion of a sample extracted from naturally occurring mineral growth such as might be made from a rock sample 38 in FIG. 1.

Sample 310 consists of a cut section having a thickness of approximately 0.03-1.0 millimeter which is polished on both sides and which is mounted on a glass slide (not shown in FIG. 1). The view of FIG. 1A is a view of the polished section as seen through a microscope and is, thus, greatly enlarged. The approximate scale can be indicated in that substantially all of the fluid inclusions, like inclusion 312, formed in the various mineral growths in sample 310 are under 10 microns in diameter. Sample 310 includes a plurality of mineral growths, like minerals 314, 316, 318, 320, 322, and 324. Minerals 316 and 318 each include a mineral overgrowth 326 and 328, which acts as and is referred to as a cement.

Mineral 324 includes therein a plurality of primary inclusions, like inclusions 330 and 332. These inclusions were formed during the initial growth of mineral 324. A healed crack 334 is formed in mineral 324, and a healed crack 336 is formed in mineral 322 and in mineral 324. Crack 334 was formed in mineral 324 after the original growth of mineral 324, and thus after the primary inclusions, like inclusions 330 and 332 were formed. Crack 336 was also formed in minerals 322 and 324 after the formation of the primary inclusions in both minerals 322 and 324. Each of cracks 334 and 336 have a plurality of secondary inclusions, as shown, formed therealong. These secondary inclusions were formed during healing of cracks 334 and 336 when mineral growth developed in the cracks. It is to be appreciated that the secondary inclusions in crack 334 trap environmental fluids at a later time than the primary inclusions in mineral 324 and the secondary inclusions along crack 336 trap such fields at a later time than when the environmental fluids were trapped in the primary inclusions in both minerals 322 and 324. Moreover, the secondary inclusions in crack 334 may well be formed at a time far removed from those formed in crack 336, and thus, the secondary inclusions in crack 334 may be of a different generation than those along crack 336. Likewise, the primary inclusions formed in the various minerals and cements in sample 310 may be formed at vastly different times from one another, thus trapping the environmental fluids present at the time of formation.

In accordance with the invention, these various classes and generations of fluid inclusions are indiscriminately opened and fluid inclusions released. Preferably, all or substantially all or at least a preponderance of the fluid inclusions are opened and volatiles released.

A sample contains typically only a fraction of a gram and, since inclusions are formed on an ongoing basis, represents an integration of the burial history over time which may, however, differ considerably from another sample just a few inches away.

Each sample is best compared to many other samples to obtain information reliable for hydrocarbon exploration. Thus, each fluid inclusion composition region has a characteristic fluid inclusion composition over a plurality of locations in the earth. Comparison of only a few samples leaves too much uncertainty regarding whether or not individual observations are typical of the formation. Reference to FIGS. 7, 8, and 10 below show that there is significant scatter in the data and therefore, that large numbers of samples are required to reliably identify trends. For FIGS. 7, 8, 10, the rate of sampling the subsurface is about every 60-90 ft. From 50-10,000 or more samples are analyzed for each stratigraphic investigation, preferably 100 to 500 or more to obtain statistically and stratigraphically reliable data sets. Samples are preferably taken at least every 200 ft, 100 ft, 50 ft or less. Sixty-foot spacing has provided excellent results in many runs. More frequent sampling can also be advantageous. Referring again to FIGS. 7, 8, 10, it will be appreciated that each zone represents a plurality of samples:

TABLE

| Zone | Figure | Approx. No. of Samples |
|------|--------|------------------------|
| 150  | 8      | 15                     |
| 152  | 8      | 8                      |
| 154  | 8      | 50                     |
| 156  | 8      | 10                     |
| 158  | 10     | 7                      |
| 160  | 10     | 7                      |

Generally, experience indicates that zones can be reliably determined when each zone is characterized by at least 5 samples, and of course, more samples improve reliability and fewer samples can also be used in cases where data scatter permits.

Collective fluid inclusion volatile composition data can be inspected for trends across a domain being stratigraphically mapped. For stratigraphic mapping, the samples are selected to span a domain in a sedimentary basin. Each well in the domain can then be examined as described in the preceding paragraph and the results can be displayed across the domain or even a particular formation in the domain.

The samples can be washed drill cuttings, cores, outcrop samples, soil samples, and the like. Drill cuttings are widely available and allow investigation of substantially the entire length of a borehole. Further, drill cuttings have been archived from many existing wells so that new wells or samples are often not needed. A rock sample of about 10 cubic centimeters or even less permits numerous runs, if desired, since only a portion of a cubic centimeter is needed for each run.

For domain studies, multiple spaced apart wells can be sampled along substantially the entire depth or along a zone of particular interest, for example, a particular formation, in several wells. These domains of analysis are in sedimentary basins and provide information about geological formations adjacent each of the wells surveyed in an area. 50 to 100 or more samples spanning a domain or interest are selected and analyzed to determine fluid inclusion composition.

According to the invention, the collective volatiles are preferably obtained by impacting each rock sample, as described below in detail, since this releases both liquid and gaseous inclusion contents. Other techniques can also be used, for example, heating, for example using a heating robe on one of rams 50 described below or by laser. Due to the relatively small number of moles of gas present, such techniques are generally ineffective for opening gaseous inclusions, although they work well for liquid-filled inclusions. Heating also may cause noninclusion gases to be evolved.

Referring now to FIG. 1, FIG. 1 illustrates in exploded view a system including a controller for releasing, delivering and analyzing composition of a plurality of fluid inclusion volatiles sample. The apparatus comprises releasing means 10 for sequentially and individually impacting and deforming each of a plurality of sedimentary rock samples effective for releasing a collective fluid inclusion volatiles sample from each analytical means 12 for determining composition of each fluid inclusion volatiles sample as it is being released, delivery means 11, 27, 28 for delivering each fluid inclusion volatiles sample from releasing means to analytical means as it is being released, and controller means 16 for causing a collective fluid inclusion volatiles sample to be sequentially and individually released by the releasing means 10 (also referred to herein as autosampler 10) and for causing each collective fluid inclusion volatiles sample to be sequentially and individually analyzed by the analytical means 12 as it is being released.

FIG. 1 illustrates an autosampler 10 controlled by controller 16 and providing collective fluid inclusion volatiles samples for each of a plurality of rock samples to mass spectrometer 12. A vacuum pump 14 places autosampler 10 under a vacuum at the start of a sequence of analyses. Thereafter, the system is maintained under vacuum by pumps 15' associated with the mass spectroscopic system. See FIG. 3A.

Auto-sampler system 10 includes upper housing 27 and lower housing 28 having seal 30 therebetween for forming evacuable chamber 60 (see FIG. 2) when housings 27 and 28 are aligned and joined. Seal 30 can be an oxygen-free high conductivity copper gasket. Housings 27 and 28 can be adapted with knife edges for sealing by engaging gasket 30. A new gasket can be used for each run. The evacuable chamber has an outlet 11 with valve 11$v$ and functions for delivering released volatiles to analysis as they are being released.

Upper housing 27 has a plurality of linear vacuum feedthroughs 19, 21, 23, and 25 for permitting shafts from pneumatic rams 18, 20, and 22 and motor 24 to pass into chamber 60 (see FIG. 2) without loss of vacuum. Each of rams 18, 20, 22, and motor 24 have a housing with a flange 18$f$, 20$f$, 22$f$, 24$f$, respectively, for sealingly mating with flanges 19$f$, 21$f$, 23$f$, and 25$f$ of the linear feedthroughs. Motor 24 can be a stepper motor or a servo motor with a shaft encoder or any motor capable of having the shaft position controlled. Controller 16 can include systems as are well known for generating drive signals for motor 24 and for generating signals and driving forces for driving rams 18, 20, 22.

Lower housing 28 comprises flange 28$f$, sidewall 28$s$, and base 28$b$. Base 28$b$ has a groove 32 therein in which a plurality of bearings 34 can be placed. Circular carousel 26 is adapted with a plurality of sample chambers 36 therein and centered slot 46 for engagably receiving shaft key 44 on stepper motor shaft 42. Carousel 26 has groove 32$b$ for engaging bearings 34 in groove 32$a$ in base 28$b$. As a result, when carousel 26 is placed in lower housing 28, grooves 32$b$ and 32$a$ cooperate to align the carousel 26, and bearings 34 provide for rotation of carousel 26 in response to motor 24 turning shaft 42 having key 44 engagably connected with slot 46.

Sample chambers 36 are each effective for receiving a rock sample 38 and for maintaining it in a confined space during volatiles release between the walls and base of the chamber and the impacting means.

As illustrated, there are three pneumatic rams 18, 20, and 22 passing through upper housing 27. More or fewer rams can be used. Illustrated carousel 26 has three concentric rings of sample chambers 36, and each pneumatic ram aligns with a respective concentric ring of sample chambers. Ram 18 is illustrated with plunger 52 and ram tip 54. Ram 18 aligns with outer ring 36$o$; ram 22 aligns with intermediate ring 36$i$, and ram 20 aligns with central ring 36$c$. Thus, when a sample chamber 36 is aligned with a respective ram, the ram can be actuated to impact a sample 38 in the chamber effective for releasing a collective volatiles sample. Preferably, each sample chamber is also provided with a sample chamber slug 40 to prevent cross contamination of samples during impacting. Slug 40 can be considered part of the impacting means. Sample 38 and slug 40 are shown enlarged in circle 39 for clarity. However, slug 40 is adapted to cover sample 38 in chamber 36 while permitting volatiles to escape through an annulus between slug 40 and the wall of chamber 36. While only one slug 40 and sample 38 are shown, there will usually be as many slugs 40 and samples 38 as chambers 36.

Figure 2:
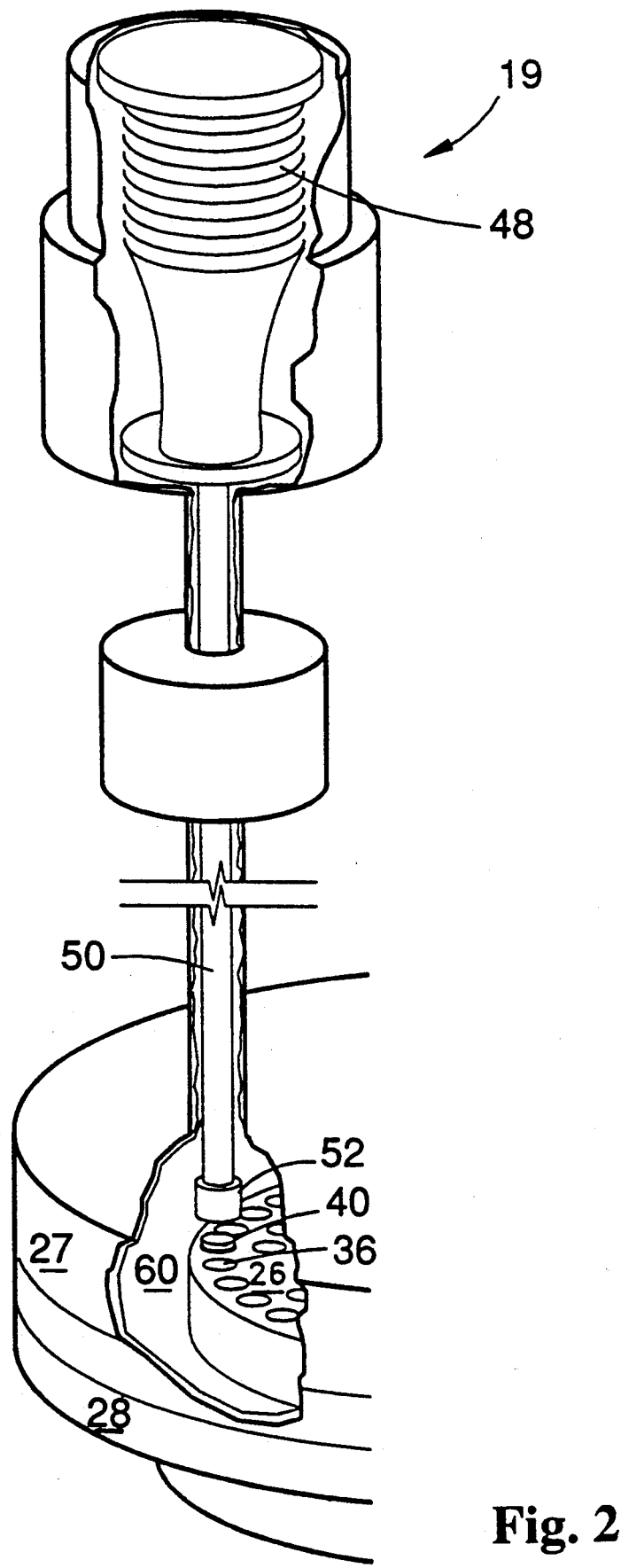
FIG. 2 illustrates a cutaway view of a portion of the autosampler 10 of FIG. 1 as assembled.

Referring now to FIG. 2, FIG. 2 illustrates in greater detail the operation of the pneumatic rams. Illustrated in FIG. 2 is pneumatic ram 19 which as indicated is aligned with the outer row 36$o$ of sample chambers on carousel 26. In response to a signal from controller 16 (see FIG. 1), the pneumatic ram bellows 48 expand, driving shaft 50 and plunger 52 into contact with the slug 40, impacting sample 38 (see FIG. 1) in chamber 36. Impacting of the sample may occur one or more times, preferably multiple times under control of controller 16 to ensure release of substantially all fluid inclusion volatiles. The released fluid inclusion gases then are transported within chamber 60 through a space between the lower surface of upper housing 27 and the upper surface of the carousel 26 to mass spectrometer 12 for analysis.

Impacting of the sample preferably occurs while the sample is closely confined by a slug 40 in a chamber 36. The impact can be any impact sufficient for releasing a collective fluid inclusions volatile sample, for example, by crushing, pulverization, and the like. Preferably, the impact is effective for causing a deformation or concussion of the sample effective for releasing a collective volatiles sample substantially without crumbling or powdering the sample. For most drill cuttings run, an impact of about 400 pounds per square inch is effective. In this way, creation of new surfaces on which adsorption of released volatiles can occur is minimized. The result of crushing is preferably a rock sample deformed and shaped by the sample chamber and the crushing means into a compacted aggregated mass.

Impacting can take place virtually instantaneously up to about 10 seconds or even longer. Ten seconds has provided highly satisfactory results. In such case, the plunger impacts the rock sample and maintains deforming fluid inclusion pressure thereon for 10 seconds, for example. When iterative impacting is employed, all of the iterations can be made to occur in 10 seconds or less if desired. Impacting can be for a time effective for releasing a volume of fluid inclusion gasses. Release of substantially all, or at least a preponderance of, fluid inclusion volatiles is preferred.

As illustrated, the invention includes a controller 16 for controlling sampler 10, for example, by controlling motor 24, rams 18, 20, 22, to release sequentially in bulk from each of a plurality of rock samples fluid inclusion components and for controlling mass spectrometer 12 for removing and analyzing the released fluids.

Figure 3A:
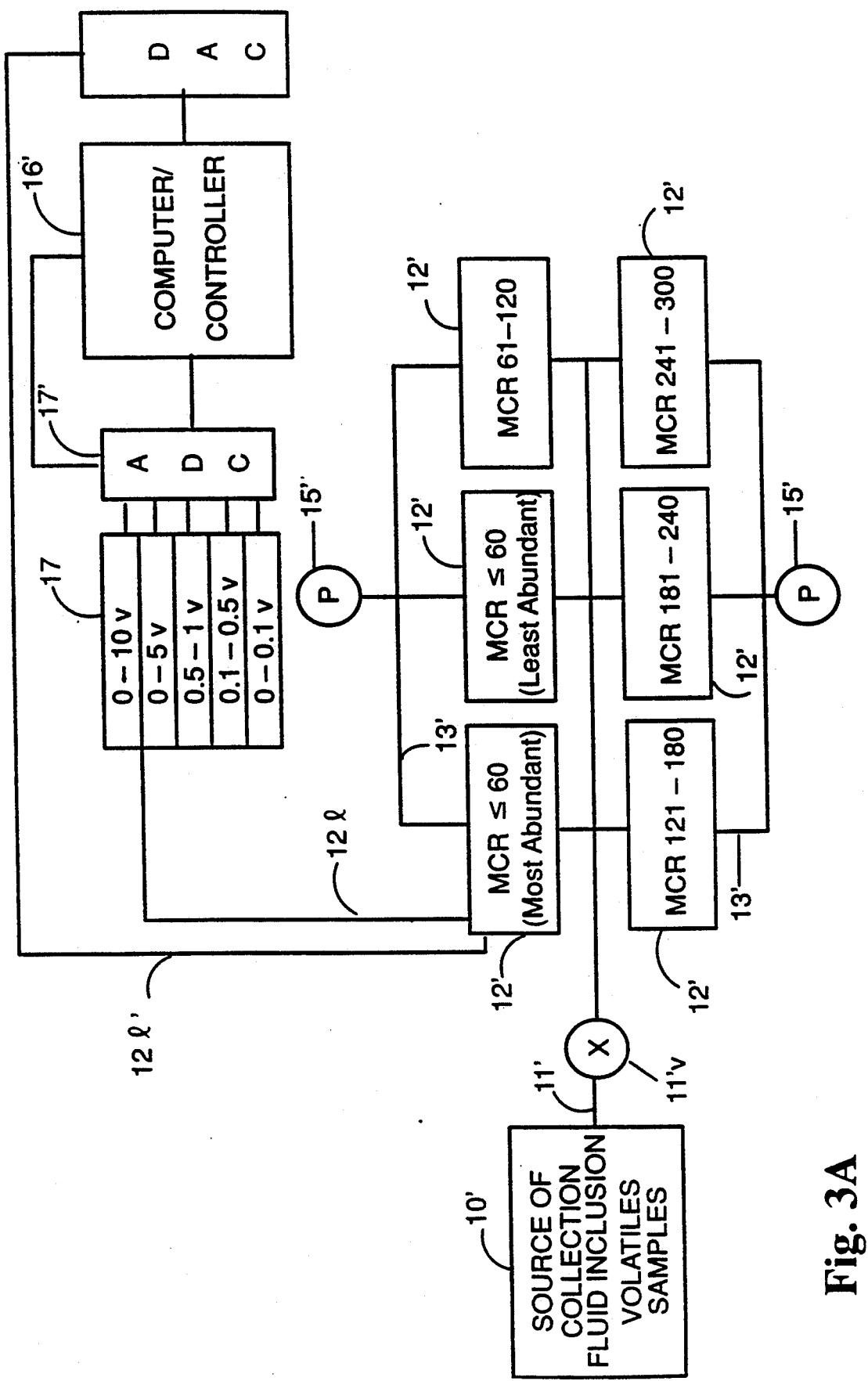
FIG. 3A illustrates a system for mass spectroscopic analysis of collective fluid inclusion volatiles samples.
Figure 3B:
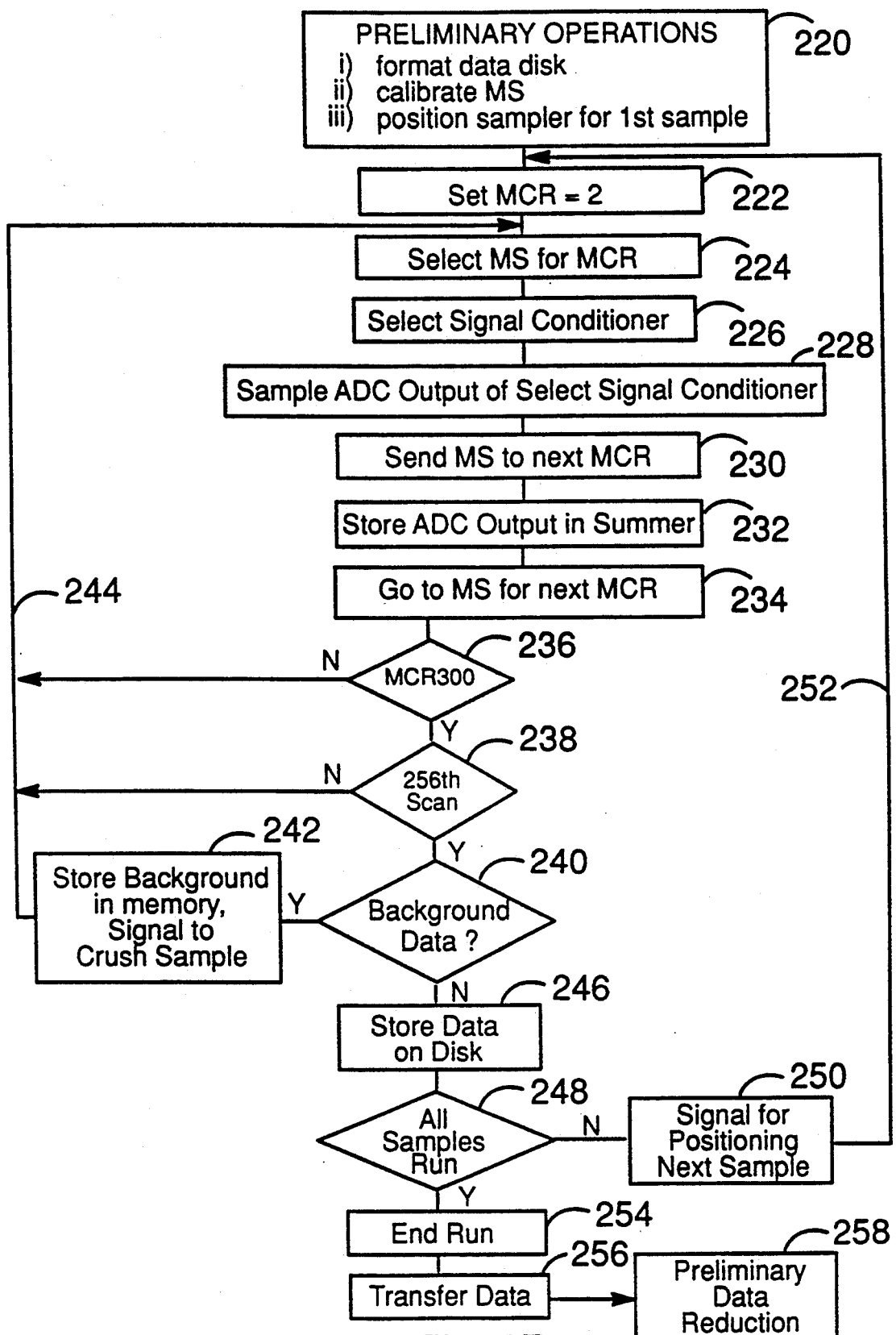
FIG. 3B illustrates, by a simplified flow diagram, control of the autosampler/analysis system of FIGS. 1 and 3.

Controller 16 is described in more detail in reference to FIG. 3B.

Controller 16 can be, for example, a personal computer programmed for controlling the autosampler and for storing composition data produced from mass spectrometer 12 on disk together with apparatus for driving the rams, motor, controlling mass spectrometers and the like. Such equipment is well known and can readily be assembled by those skilled in the art for the invention. Use of a personal computer for such control is described herein but any suitable controller can be used.

As indicated at 220 in FIG. 3B, certain preliminary operations can be controlled by controller 16. Thus, controller 16 can generate signals for formatting a data disk in controller 16, for calibrating mass spectrometer system 12, and for positioning carousel 26 for analysis of a predetermined first rock sample.

For each rock sample, controller 16 generates signals causing measurements and recording of background data, causing a rock sample to be impacted, causing measurement and recording of background plus fluid inclusion volatiles, causing storing of preliminary recorded data on disk and querying whether all samples have been run. If all samples have not been run, controller 12 generates a signal controlling motor 24 for causing carousel 26 to position for crushing of the next rock sample. When all samples have been run, controller 12 can perform end of run procedures such as releasing the vacuum on the system, data transfer, and the like. The operation of controller 16 is illustrated in more detail in FIG. 3B discussed below.

Rock Samples

Washed cuttings, core, outcrop samples, even soil samples collected at various locations in or on the earth, can be analyzed. Percussion sidewall cores are currently not preferred due to grain fracturing, resulting in inclusion breakage, during coring. As discussed in reference to FIGS. 5A and 5B below, the invented method discriminates inclusion from noninclusion gases, and frequently it does not matter if cuttings are from a well drilled with oil or from one drilled with water based muds. Sometimes, however, the background levels given off by some cuttings from wells drilled using oil based muds is so high as to mask response from opening the inclusions. Drilling and other fluids present in the pores or adsorbed on the rock, such as formation fluids occurring in the rock's pore system, may be removed before release of fluid inclusions to reduce background levels. Extraction of drilling mud residues in solvent appears to eliminate the problem, but is rather expensive and may take weeks or months for the several hundred samples that may be used in a single inclusion study. However, the preferred technique for opening the inclusions, described below, discriminates inclusion from noninclusion gases in most cases. Further, heating for example at 200° C. in air overnight prior to analyses often reduces background to acceptable levels.

The technique can be used on carbonates, clastics, and sandstones.

A typical rock sample is less than 10 cc (cubic centimeters) in volume which provides sufficient material for several runs, if necessary. Core and outcrop samples are usually broken prior to analysis while drill cutting samples can be poured directly into the sample holes. Individual samples for analysis generally range from about 1/100 to about ½ cc, typically about 1/25 to about ½ cc.

For single well profiles, a cuttings sample for every 60 to 90 ft can be analyzed. More frequent sampling can be used across zones of particular importance. The samples are preferably not composited, that is, drill cuttings from different footages are not combined although composited samples can be used if desired. The frequency of core and outcrop samples, for example every 10–20 ft, depends on the scale of the problem being addressed and the availability of material. Broadly intervals between 1 and 200 ft are preferred.

Analyses

Samples are analyzed using the fluid inclusion autosampler. Samples 38 are loaded into carousel 26 containing sample holes 36. Steel slugs 40 are placed in holes 36 on top of the samples. During analysis, slugs 40 are rammed by plungers 50 having ram tips 52. Slugs 40 ensure the entire sample is impacted and prevent intersample contamination from scattered bits and pieces. Depths are recorded by entry into a computer such as controller 16 as the samples are loaded into predetermined sample chambers in the carousels. The depths can later be transferred to another computer such as a mainframe for analysis of resulting data if desired.

The loaded carousel 26 can be heated at 200° overnight prior to analyses to drive off most of the absorbed water and other volatiles, reducing pump down time in the vacuum system. Loaded carousels 26 can then be removed from the drying oven and loaded into lower housing 28. In pumpdown configuration valve 13v in line 13 is open and value 11v in line 11 is closed; in automated sampling configuration, 11v is closed and 13v is open. Autosampler 10 can be heated to maintain the samples at about 150° C. during operation. Inlet and outlet lines to mass spectrometer system 12 can also be heated to about 150° C.

Generally, the analysis temperature can be any temperature effective for volatilizing particular molecules of interest up to a temperature less than that at which thermal decrepitation causes release of fluid inclusion volatiles. For oil and gas exploration, temperatures in the range of about 150° to about 200° C. are particularly advantageous for volatilizing of hydrocarbons.

Autosampler 10 is then evacuated, for example, first to very high vacuum using a turbomolecular pump such as pump 14 not open to the mass spectrometers. The entire system can then pump down in its analytical configuration, for example, for a period of time, for example, three hours before the analytical session is begun. When the system is in analytical configuration, released inclusion volatiles from autosampler 10 can be pumped directly through mass spectrometers 12 (See FIG. 3A). That is, gas evolved during analyses must be pumped through the ionization chambers of the mass spectrometers in order to be pumped away. This can be seen more clearly in FIG. 3A.

The system is maintained at a vacuum of about $10^{-8}$ to about $10^{-6}$ torr. Even during release of volatiles, the vacuum will not decrease much below $10^{-6}$ torr. Generally, the pumps evacuating the system during analytical configuration maintain low pressures to insure substantially all of released volatiles are passed through mass spectrometers for analysis.

Autosampler 10 is depicted in FIGS. 1 and 2. A circular groove 32 in the base of carousel 36 rests on ball bearings 34 that rest in a circular groove in the bottom plate of lower housing 28. Asymmetric tab 44 fits into the notch 46 in the carousel. Asymmetry of the tab and notch assure that the sample tray is correctly positioned in the autosampler so that each sample has a uniquely determined position relative to the sampler. Upper and lower housings 27 and 28 of autosampler 10 are fastened together. Oxygen-free high-conductivity copper gasket 30 is inserted between the two halves prior to connecting them. Vacuum seal is made by steel knife edges in both the upper and lower halves cutting into the gasket. Preferably, no hydrocarbon components are used anywhere in the system.

Motor 24 under control of controller 16 via line 12c drives the shaft 42 that turns the asymmetric notch 44 that turns carousel 36. As illustrated, there are three impact assemblies, one for each of the three sample rows. Each sample, in turn, is placed under one of the impactors.

FIG. 2 shows a cut away view of impactors positioned over a sample with autosampler 10 sealed. The impactor can be a stainless steel bellows 48, which transmits linear motion generated outside the vacuum chamber to shaft 50 inside the vacuum chamber 60. Bellows 48 can be driven from above by an air piston which can be included in controller 16 for both lowering and raising belows 48. Ramming tip 52 covers the end of shaft 50. Shaft 50 is positioned directly overhead of slug 40 that rests on top of rock chips 38, as shown in FIG. 1. The sample is now ready to be analyzed.

FIG. 3A illustrates mass spectrometic analysis of collective fluid inclusion samples in accordance with the invention.

Referring now to FIG. 3A, there is illustrated a source 10' of collective fluid inclusion volatiles samples, such as autosampler 10 in FIG. 1, connected via line 11' having valve 11'v to a preferred arrangement of mass spectrometers 12'. During analytical configuration, valve 11'v is open and samples are being withdrawn as they are released by crushing. Thus, the system depicted in 3A is dynamic, i.e., open to the sampler 10' during sample release. As illustrated, the mass spectrometers are arranged in two banks of three, each bank having a pump 15' for drawing sample from line 11' through each of mass spectrometers 12' via outlet line 13'. Each mass spectrometer is configured to sample a specific set of MCR responses using the optimum gain for each, for example, as follows:

| Mass Spectrometer | Mass to Charge Ratio Responses Sampled |
| --- | --- |
| 1 | 2,16,17,18,28,44 |
| 2 | 3,4,12,13,14,15,19–27,29–43,45–60 |
| 3 | 61–120 |
| 4 | 121–180 |
| 5 | 181–240 |
| 6 | 241–300 |

There are generally no peaks at MCR 5 to 11. Those skilled in the use of MS will appreciate that by assigning specific MS to samples, a set of MCR responses which have comparable amplitudes, time lost in switching amplifiers for the MS can be minimized. Thus, MS1 samples the most abundant MCR<61 and MS2 samples the least abundant MCR<61.

The 0–10v signal outline of each mass spectrometer 12' is operably connected to a bank of five signal conditioners 17', each configured for a different optimum gain, for example, as follows:

| Signal Conditioner | Gain Configuration |
| --- | --- |
| 1 | 0–10 v |
| 2 | 0–5 v |
| 3 | 0–1 v |
| 4 | 0–0.5 v |
| 5 | 0–0.1 v |

The outputs of signal conditioners 17 are provided to analog to digital converter (ADC) 17' and then to computer controller 16'. For simplicity, only the output of one MS 12' is illustrated but the other MS 12' are also so configured.

As indicated, the MS system of FIG. 3A is open to sampler 10' during sampling. This minimizes residence time of volatiles in the sampler 10' but means that volatiles are being passed through the MS system over a period of time dependent on the relative molecular weight of the volatiles and the period of time when volatiles are being released from a particular sample. For example, the rate of travel of volatiles is molecular weight dependent so that lighter volatiles are analyzed before heavier volatiles. Also, where sampler 10' is an autosampler 10 according to another aspect of the invention, impacting the sample to release volatiles takes a discrete amount of time and if multiple impacts are used, there can be a series of releases of volatiles for analysis of a single rock sample.

According to aspects of the invention, it is desirable to have a record of MCR for a rock sample which reliably permits comparison of compounds represented by one or more MCR to one or more others.

According to an aspect of the invention, there is provided an MS system for producing such a reliable record. The MS system is configured and controlled for scanning a range of MCR of interest a multiplicity of times during the period of release of volatiles from each rock sample, and the results from all the multiplicity of scans are summed on an MCR by MCR basis for each rock sample.

As described herein, the MCR range of interest is from about 2-300 MCR to encompass an advantageous range for analysis. Greater or lesser ranges can also be used. As indicated, the MS system is configured to sample the most abundant MCR using a single MS to avoid lost time due to amplifier switching. As described herein, the multiplicity of scans is 256. More or fewer scans can be used. However, reduction in number of scans leads to loss of precision and accuracy. Hence, more rather than fewer scans are desirable.

Referring now to FIG. 3B, FIG. 3B illustrates control of the MS system of FIG. 3A integrated with control of the autosampler 10 of FIG. 1. Generally, the system scans a sampler 10', a multiplicity of times during a time when no sample is being released and sums the results on an MCR by MCR basis. The system then scans a sampler 10' a multiplicity of times during a time when a collective volatile sample is being released from a particular rock sample and sums the results on an MCR by MCR basis. The system repeats the preceding two steps until a plurality of samples has been run. In a preliminary data reduction step, background readings taken before each sample is read can be removed from the sample readings. The preliminary data reduction is described in more detail in reference to FIGS. 5A and 5B.

Referring now to FIG. 3B in detail, FIG. 3B illustrates a system for control of sampler 10 and the MS system of FIG. 3A using a personal computer in which data are stored on disk and later transferred to another computer for analysis. Clearly, other controller systems for use with the invention are also available and the invention is not limited to the particular computing hardware described.

Step 220 is for performing certain preliminary operations such as formatting a data disk, calibrating the MS, and positioning carousel 26 for crushing of the first sample.

Step 222 is for setting the beginning of the MCR range MCR=2. Step 224 is for controller 16 sampling the output of the MS configured for MCR 2 and step 226 is for the computer selecting a signal conditioner for optimum gain for MCR 2 signal and causing the selected conditioner output to appear on the output line of ADC 17' where the computer samples it (step 228). Step 230 is for sending the MS to the next MCR to be tested. This can be accomplished, for example, using a digital to analog convertor in controller 16. See Table supra for a particular assignment of MCR to mass spectrometers. Step 232 is for storing the sampled ADC in the appropriate summer. Steps 234 and 236 are for the computer sampling in the same way via loop 244, the MS assigned to the next MCR until the full range of MCR, as illustrated, MCR 2-300 has been scanned.

The step for sending the appropriate MS to the next MCR is illustrated in FIG. 3A by line 121 and in FIG. 3B by step 230. It can be accomplished using controller 16 including a DAC (digital to analog converter). Thus, a personal computer can provide a signal selecting the next MS for the next MCR to a DAC for a particular mass spectrometer. The DAC can then cause the appropriate mass spectrometer to be configured for the next MCR to be read.

By step 238, the full range of MCR of interest is scanned a multiplicity of times for each rock sample, the data for each MCR being summed on an MCR by MCR basis for the multiplicity of scans. After 256 scans, the computer tests whether there was a scan of background data or of sample data by step 240. This can be as simple as determining the set of 256 scans as the second set since impacting the previous rock sample. Upon determining that the reading were of background data, step 242 stores the background data for the sampler in the computer's memory and generates a signal to autosampler 10 causing the first sample to be impacted and returns to step 244.

Steps 224 through 240 are then repeated and when step 240 now responds indicating that sample data have been measured, step 246 stores the sample data on disk. Step 248 inquires whether all samples have been run and if not, by step 250 and loop 252 provides a signal via line 12'l (see FIG. 1) to sampler 10 to position the next rock sample for analysis. After step 248 indicates that all samples have been run, step 254 ends the run, and the data can then be transferred (see step 256) to another computer for preliminary data reduction (see step 258). All of the steps described above can be readily implemented by those skilled in the art of computerized control from the description herein using commercially available equipment.

Figure 4:
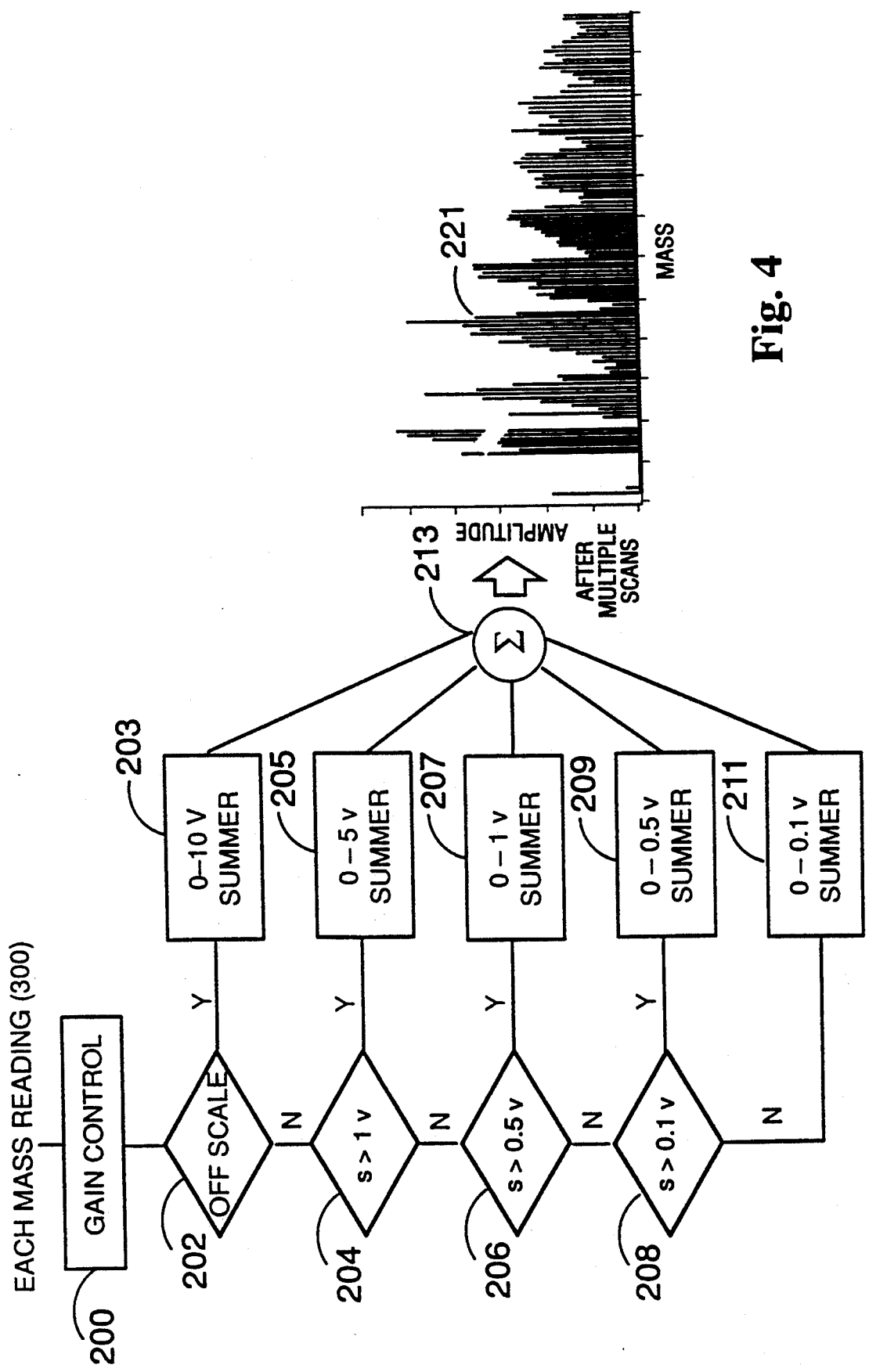
FIG. 4 illustrates, by simplified flow diagram, a system for summing mass to charge ratio (MCR) responses for each of a plurality of scans of a range of MCR for a single collective volatiles sample to produce summed MCR values for the totality of scans for the single collective volatiles sample which can be displayed as an MCR spectrogram.

Referring now to FIG. 4, an autoranging routine is shown for selecting an optimum signal conditioner for each MCR reading and for summing the readings on an MCR by MCR basis. For each MCR reading, a particular signal conditioner is selected by, for example, 0-5 v gain control 200. Then each MCR response is directed to the appropriate memory for summing by steps 202, 204, 206, 208. Thus, if step 202 indicates that the signal s for the particular MCR is >5 v, the response is sampled on the 0-10 v channel and summed using the 0-10 v summer 203. If $1 < s < 5$, step 204 samples and sums the response using the 0-5 v summer 205. If $0.5 < s < 1$, step 206 samples and sums the response using the 0-1 v summer 207. If $0.1 < s < 0.5$, step 208 samples and sums the response using the summer 209; if <0.1, using the summer 211. After, for example, 256 mass scans are summed for each mass response in the range of 2-300 mass to charge ratio units, computer 16 can sum, the MCR responses for each MCR over all scans and can generate for each collective fluid inclusion volatiles sample a mass spectrogram such as the one shown at 221 in FIG. 4. Mass spectrograms for autosampler background data and for a sample are also illustrated in a simplified manner at 132 and 136, respectively, in FIGS. 5A and 5B.

During operation, controller 16 reads the output of mass spectrometers 12' 256 times in about 10 seconds as a volatiles sample is being released from an individual rock sample to collect 256 complete MCR spectra from MCR 2 through 300, i.e., for each volatiles sample 256 scans of MCR 2-300 are made. A summer 213, for example, in computer 16, sums the 256 responses from each MCR from all of the multiplicity of scans as they are collected. A 0-10 volt signal from each mass spectrometer is sent to a bank of five signal conditioners set at different gains. The gains of the 30 signal conditioners are calibrated using a National Bureau of Standard standard. The computer uses an autoranging routine such as shown in FIG. 4 to select the optimum signal conditioner for each MCR scan. For each MCR, after selecting the optimum signal conditioner, collecting the data, adding it to the total for that MCR, and storing the result in memory, controller 16 triggers the appropriate mass spectrometer system to proceed to the next MCR. The computer then reads a signal from the mass spectrometers configured to sample that MCR, and so on until 256 MCR scans are summed. There is about 100 microseconds between each MCR sampled.

A plurality of mass spectrometers is used to sample a range of MCR's of interest in oil and gas exploration. Preferably, substantially all or at least a preponderance of ranges such as 2-60, 2-120, 2-180, 2-240, 2-300 and the like are scanned a multiplicity of times as a volatiles sample is released from each rock sample.

For each rock sample the summed data from the first multiplicity of scans are an analysis of the background gases in the system (see 130 in FIG. 5A). These gases result from the breakdown of hydrous minerals as well as the release of volatiles adsorbed on the rocks as well as residual gases remaining behind from previous samples. All rock samples as well as the autosampler and the rest of the vacuum system contribute to the system background.

Once the background is characterized, the computer signals and controls the appropriate air piston one or more times to ram the appropriate steel slug thus impacting the sample (time of occurrence illustrated in FIG. 5A by arrow 134). 256 new scans of 2-300MCR are initiated each time the rock sample is impacted or while the rock sample is crushed multiple times. Most of the fluid inclusions in the sample are broken by this process and release their gas into the vacuum system. The sum of the second and subsequent multiplicity of 256 scans is the analysis of the fluid inclusion gases plus the background, as illustrated by reference numeral 136 in FIG. 5A.

Referring now to FIG. 5B, FIG. 5B illustrates a preliminary data reduction step in which the background gas contribution 132, characterized immediately before impacting each rock sample, is subtracted from data 136 on an MCR by MCR basis for each collective fluid inclusion volatiles sample plus background. This technique is effective for discriminating inclusion from noninclusion gases so that the final volatiles record is representative of inclusion gases.

This is a gas analysis; there is no carrier fluid. The analyses of each sample take about 25 seconds. A short period of time, for example, ninety seconds, can be allowed between samples for the system to pump away as much of the released inclusion gases as is practical. Many substances which are liquids at room temperature and pressures are gases under ultra high vacuum and 150° C., such as water and gasoline range hydrocarbons. Very long chain hydrocarbons, however, remain liquids even under these conditions, and therefore, are typically not analyzed.

Mass Spectrometry

The composition data used for stratigraphic mapping of subsurface structure are preferably the results of mass spectrographic analyses of the volatile contents of fluid inclusions released in bulk from rock samples. Apparatus and techniques for quickly and efficiently producing samples of bulk volatiles are described above.

In the mass spectrometer, the molecules in each bulk sample are ionized, accelerated, separated according to MCR, and measured. Ionization is usually accompanied by partial fragmentation of the molecules which is characteristic of specific molecules and operating conditions. While fragmentation complicates interpretation—a given molecular weight fragment can be derived from different molecules—it also permits distinguishing between isomers and gives molecular structural information. The output can be various forms of MCR versus abundance records, mass spectrograms, and the like.

Although mass spectrometry is preferred, other techniques, for example, chromatographic (GC), a gas chromatographic/mass spectrometry analysis GC/MS can be used.

Compared to MS, GC and GC/MS analysis are relatively slow, requiring as much as an hour per sample. MS analyses takes only 24 seconds per sample, with ninety seconds of self-imposed pumpdown between samples. Stratigraphically and statistically large data sets are necessary using fluid inclusions to aid in locating subtle traps having reservoired hydrocarbons and to map hydrocarbon migration pathways and barriers.

Mass spectrometry analyses many gases not analyzed by GC and GC/MS. In particular, gases diagnostic of paleo subaerial exposure zones, such as $O_2$, $N_2$, Ar, Ne, and Xe are not analyzed by these other techniques. Yet, this information may be critical in subsurface correlation and burial history reconstructions. Other gases not typically analyzed with GC and GC/MS include $CO_2$ and $H_2O$, the two most abundant gases in fluid inclusions. Ammonia, sulfate, HCl (a possible salinity indicator), methane and other light hydrocarbons, and $H_2$ are usually not analyzed. In some reservoirs, the only constituents of note are methane, $CO_2$, and $H_2S$. $H_2$ has been found to be a useful indicator of thrust faults in some basins and a stratigraphic correlation marker in others.

Aqueous inclusions may contain water soluble hydrocarbons that may be oil proximity indicators. These inclusions would not be considered if fluid inclusion investigations were restricted to samples having large abundant oil inclusions.

MS also discriminates between noninclusion and inclusion derived gases. Such discrimination is not possible using GC or GC/MS. Fluid inclusion samples analyzed using these other techniques must be virtually absolutely clean in order to avoid analysis of contaminants, requiring much more sample preparation.

One reason why fluid inclusion efforts have previously failed to provide significant and widespread benefit to exploration is because these efforts were often based on techniques, such as GC/MS and Laser-UV fluorescence microscopy, that are applicable only to small numbers of samples and are only useful for those samples having large and abundant oil inclusions. All samples contain fluid inclusions that can be analyzed using mass spectrometry, and the stratigraphic analyses of fluid inclusion mass spectra has provided useful information, regardless of the presence of abundant oil inclusions.

The mass values of some fragments encountered in fluid inclusion analysis and source molecules are shown in the following table.

MCR Signatures - Inorganic Fluid Inclusion Gases

TABLE 1

| Inorganic Gases | MCR Signature |
|---|---|
| H | 2 |
| He | 4 |
| $H_2O$ | 18 |
| $CO_2$ | 22,44 |
| Ar | 40 |
| $N_2$ | 28,14 |
| $NH_3$ | 17 |
| CO | 28 |
| $H_2S$ | 34 |
| $O_2$ | 32 |
| SO(1-3) | 48 |
| COS | 60 |
| $CS_2$ | 76 |
| Ne | 20,22 |
| HCl | 35,36,37,38 |
| Xe | 129,130,131,132,134,135 |

Mass Signatures - Organic Fluid Inclusion Gases

TABLE 2

| Organic Gases | Mass Signature |
|---|---|
| Methane | 15 |
| Ethane | 30 |
| Propane | 44 |
| Butane | 58 |
| Benzene | 78 |
| Toluene | 91 |
| Xylene | 105 |
| Triterpenes | 191 |
| Steranes | 217 |

The mass spectra for the higher mass organic compounds becomes very complicated with many overlapping mass spectra peaks, making it difficult or impossible to identify single compounds with certainty. Classes of organic compounds, however, share common fragments:

MCR Signatures - Higher Mass Organic Compounds

TABLE 3

| Organic Gases | MCR Signature |
|---|---|
| paraffins | 57 |
| naphthenes | 55 |
| aromatics | 77 |
| toluene | 91 |
| alkylated naphthenes | 97 |

In addition to these peaks, these hydrocarbon families tend to give responses at every 14 mass numbers due to the CH2 repeat in organic polymers:

MCR Signatures - Higher Mass Organic Compounds With Repeating $CH_2$

TABLE 4

| Organic Gases | MCR Signatures |
|---|---|
| paraffins | 57,71,85,99,113,127, etc. |
| naphthenes | 55,69,83,97,111,125, etc. |

In the higher mass organic compounds, quantitative analyses of individual compounds are not as important as identifying characteristic regions or zones of fluid inclusion composition (fingerprinting the regions) using fluid inclusion composition data. Such identification of regions in the subsurface requires a plurality of samples from a respective plurality of locations in the earth for characterizing each region. Once a class of inclusions is fingerprinted, its distribution in the earth can be mapped.

Referring now to FIG. 6, FIG. 6 illustrates results of analysis of a sample after autosampler back ground has been removed. FIG. 6 shows a mass spectrum for a collective sample to be composed of a multitude of peaks at various MCR peaks. This is not only the result of there being a large number of compounds in the inclusions, but also because compounds dissociate or "crack" during ionization by electron bombardment in the mass spectrometer. For instance, the molecular weight of water, $H_2O$, is 18. However, water has a characteristic cracking pattern resulting in contributions on masses 17 (OH), 16 (O), and 2 ($H_2$). $CO_2$ has its main contribution on mass 44, but also has major contributions on 28 (CO), 16 (O), and 12 (C) as well as 22 ($CO_2$++). Methane, $CH_4$, has a molecular weight of 16, and methane's main peak is on 16, but water and $CO_2$ also have major O contributions on 16. Therefore, it is difficult to derive methane content directly from mass 16, especially in a situation with a small amount of methane in the presence of large amounts of $H_2O$ and or $CO_2$. However, methane also has a peak at 15 ($CH_3$), which is free from O interference. Although higher alkanes also have a contribution on 15, their contribution to that peak is minor, so 15 is considered to be a clean, i.e., relatively free from interferences, methane peak.

FIG. 6A also illustrates the occurrence of recurring peaks at about 14 MCR unit intervals. Such recurring peaks are not observable in the linear display of FIG. 6B, but are advantageous in investigating the subsurface. See EXAMPLE I below.

FIG. 6, as indicated, is a logarithmic display of MCR abundance in a collective volatiles sample resulting from summing a plurality (256) of scans of MCR 2-300 for each sample. Both the logarithmic record and the multiple scanning of each sample facilitate identifying the abundance of the trace elements and compounds useful in accordance with the invention for inclusion mapping the earth's subsurface.

This can be illustrated by reference to FIG. 6B which shows the data of FIG. 6A displayed using a linear scale. FIG. 6B shows that MCR at 16 (representing oxygen), 17 (representing ammonia $NH_3$), 18 (representing $H_2O$), 14,28 (representing nitrogen $N_2$), 22,44 (representing $CO_2$), are the most abundant inorganic volatiles in sedimentary fluid inclusions. A methane peak at MCR 15 and other minor hydrocarbon peaks can be observed. It will be apparent that it is useful according to the invention to use a nonlinear, for example, logarithmic scaling of the MCR data to enhance MCR responses of trace organic and inorganic volatiles relative to the more abundant components of fluid inclusions.

According to a further aspect of the invention, composition data resulting from analysis of collective fluid inclusion volatiles are displayed as a function of depth along a borehole in the earth. Since the composition data are representative of heterogeneous fluid inclusions, MCR can be selected representative of particular compounds of interest and displayed relative to other MCR. Such displays may be referred to as fluid inclusion composition log displays.

In comparing one or more types of molecules to one or more others, such as A to B, it is preferred to determine the ratio A/(A+B). This permits a semiquantitative evaluation from well to well. A is said to be normalized with respect to B. Either A or B can represent one or more MCR.

Different displays are useful for different purposes as described in more detail below. Generally, binary displays in which one MCR or group of MCR is compared to another MCR or group of MCR are used for fluid inclusions log displays. Such binary displays are useful as displaying relative abundance of one or more compounds to one or more others. Referring to FIG. 1, by measuring and integrating a pressure change during volatiles release, for example, using pressure gauge P, a measure of absolute abundance of the various MCR can also be obtained using the ideal gas law.

Table 5 illustrates some useful binary displays; however, many other selections for display of relative or absolute abundances of elements and compounds in fluid inclusions can be used in accordance with the invention. Exemplary mapping uses are shown in Table 5; however, all measures can be used as chemical compartmentalization markers in appropriate cases.

Binary Mass/Mass Plots

TABLE 5

| Mass/Mass Ratio | Compound/Compound | Mapping Tool Example |
|---|---|---|
| 57/57 + 15 | Paraffin/Paraffin + Methane | Oil vs. Gas |
| 57/55 + 57 | Paraffin/Paraffin + Naphthenes | Oil vs. Water Inclusion |
| 91/97 + 91 | Toluene/Alkylated Naphthenes | Composition of Hydrocarbon in Inclusion |
| 34/15 + 34 | $H_2S$/Methane | Productive Faults |
| 34/44 + 34 | $H_2S/CO_2$ | Productive Faults |
| 15/18 + 15 | Methane/Water | Hydrocarbon vs Water |
| 57/44 + 57 | Paraffin/$CO_2$ | Migration Zones, Seals |
| 4/4 + 2 | Helium/Hydrogen + Helium | Stratigraphic Marker |
| 28/44 + 28 | Nitrogen/$CO_2$ | Paleo Air Zones |
| 15/59 + 15 | Methane/Methane + $CO_2$ | Migration Zones, Seals |
| 40/40 + 41 | Argon 40/Hydrocarbon fragment | Paleo Air Zones |

Referring now to FIG. 8, FIG. 8 is referred to here to illustrate a binary log display by depth.

FIG. 8 illustrates variation in mass 15 (methand) to the sum of masses 15 and 44 (methane plus $CO_2$) as a function of location along a borehole. Reference to Table 5 above will indicate that such ratio is indicative of variation in abundance of methane, specifically abundance of methane relative to $CO_2$, the most prevalent inorganic gas in fluid inclusions.

Another useful form of display is the ternary diagram in which three MCR or groups of MCR for a plurality of fluid inclusion samples are displayed relative to one another. Useful ternary displays are set forth in Table 6 below; however, many others can be selected in accordance with the invention.

Ternary Mass/Mass/Mass Plots

TABLE 6

| Mass/Mass/Mass | Compound/Compound/Compound |
|---|---|
| 12/28/44 | $CO/N_2/CO_2$ |
| 91/97/15 | Toluene/alkylated Naphthene/Methane |
| 34/44/15 | $H_2S/CO_2$/Methane |

Referring now to FIG. 7, FIG. 7 illustrates a ternary mass/mass/mass display of collective fluid inclusion samples along a borehole. Ternary diagrams are useful particularly for recognizing chemical compartment signatures or fingerprints since they are readily recognized visually. Side 180 represents the ratio of MCR representative of paraffins to MCR representative of toluene (paraffins/(paraffins plus toluene)); side 182 represents the ratio of MCR representative of methane to MCR representative of methane plus toluene; and side 184 represents the ratio of MCR representative of methane to MCR representative of methane plus paraffins.

Each of symbols 186, 188 represent a sample at a depth along a borehole locating the methane, paraffin, toluene components relative abundance in the ternary plot.

Symbols 186 are clustered in a group illustrated by dashed line 190 having a characteristic definable range in the ternary plot whereas symbols 188 are clustered in a group having a characteristic definable range in the ternary plot illustrated by dashed line 192.

Group 188 is different in its ranges on the ternary plot from group 192. Group 188 is associated with deeper levels being investigated and Group 192 is associated with shallower levels. Thus, Groups 188 and 192 are representative of regions of different characteristic inclusion chemistry in the subsurface and are indicative of different geological histories for the two regions.

Once such groups are identified based on a plurality of volatiles samples from a plurality of locations in one or more wells in a region, the groups can be mapped by extent in the earth, for example, as a function of depth or areal extent or both. Moreover, the corresponding groups can be identified in other wells in the region and used as indicators of chemical compartments from well to well in an area. This is referred herein as mapping extent of zones in the subsurface each zone having characteristic inclusion composition and each zone based on a plurality of volatiles samples from a plurality of locations.

Zones having characteristic fluid inclusion compositions can be identified using various displays in variation of inclusion composition as a function of location in the earth. Such zones can be identified using either binary or ternary or other plots showing variation in inclusion composition among a plurality of fluid inclusion samples from a plurality of locations in the earth.

In a binary plot such zones can be characterized by observing intervals of depths in the subsurface characterized by relative abundance or lack of abundance of one or more elements or compounds of interest. The sequence of such zones as a function of depth is also significant and useful in correlating regions from well to well across a field or reservoir. For example, if a characteristic pattern of alternating regions of abundance or lack of abundance of a compound occur across a field, it is indicative of shared sequence of geological history across the field. Alternatively, if part of the record pattern repeats from well to well and another part does not, it is indicative of a shared history before or after some geological event, such as faulting, which can often be identified and used in exploring for oil and gas. Finally, if no part of the record pattern is common to two or more wells, it is indicative of different formation histories.

Inclusion mapping of the subsurface has been found to show that different parts of a single geological formation often have regions of significantly different inclusion compositions which are useful in exploring for oil and gas. See EXAMPLE VI below. Moreover, inclusion composition mapping can show common patterns across different formations, for example, of hydrocarbon migration. Hence, fluid inclusion mapping of the subsurface provides highly significant information to the oil and gas explorationist which is not provided by conventional stratigraphic information—information indicating which regions in a formation or across formations have shared events in geological history.

After identifying characteristic fluid inclusion regions in the subsurface, such regions can be used as stratigraphic time markers of different fluid environments. Such time markers can cut across geology strata of the same or different ages.

These aspects of the invention are illustrated in EXAMPLES I-IV below representing analysis, using the invention, of a single well.

To summarize EXAMPLES I-IV, fluid inclusion analyses of cuttings from one well indicate zones of hydrocarbon migration, suggest the presence of a seal, restrict timing of hydrocarbon migration, provide two stratigraphic time marker horizons useful on a local scale, and illustrate two widely occurring stratigraphic fluid inclusion horizons which may be useful on a worldwide basis.

EXAMPLES I-IV are the result of the analysis in accordance with the invention of 90 well cuttings samples in 3½ hours.

EXAMPLE I

Hydrocarbon Migration Zones and Seals

The fluid-rock interaction of most interest to oil and gas explorationists is hydrocarbon migration. FIG. 8 is an example of a typical fluid inclusion log, showing depth versus some aspect of fluid inclusion composition, in this case abundance of methane, specifically of methane to $CO_2$, i.e., methane/(methane+$CO_2$). This ratio has been multiplied by 100, and is therefore plotted as a percentage. The highest possible value for X on a plot of this nature is 100, and the lowest is 0. This plot contains much information about hydrocarbon migration through the rocks penetrated by the well. Methane and carbon dioxide are the two most abundant gases in the subsurface. Both are based on carbon—methane being the most reduced compound and $CO_2$ being the most oxidized compound. Compared to water, $CO_2$ is the next most abundant inclusion compound in the subsurface, but is easier to analyze. Hence, ratioing $CH_4$ to $CO_2$ provides a relative estimate of methane abundance in the subsurface which can also be used for comparing different wells in an area.

Very high values of methane relative to $CO_2$ are found between about 14,500 and about 17,000 ft as indicated by reference numeral 150. The presence of methane and other hydrocarbons in inclusions in this section of rock indicates that a fluid hydrocarbon phase migrated into these rocks, some of which was trapped as fluid inclusions. As indicated by reference numeral 152, between 13,000 and about 14,500 ft is a zone with very little methane. The lack of hydrocarbon inclusions in the section of rock 152 immediately overlying the zone 150 suggests that zone 152 is a seal. This interpretation, based on the inclusion data, is supported by the fact that the only gas show found in this well occurred in the zone 150 having methane-rich inclusions suggesting trapping of hydrocarbons by zone 152. Gas shows, of course, are representative of pore system fluids and not of inclusion fluids. An intermediate value of methane/(methane+$CO_2$) is observed between about 3000 and 13,000 ft indicated by reference numeral 154. The methane content in zone 156 from the surface to about 3000 ft is very low.

The intermediate methane content of the inclusions in zone 154 between 3000 and 13,000 ft suggests hydrocarbon migration into these depths, as well as into zone 150 between 15,000 and 17,000 ft. The lack of significant methane in zone 156 between the surface and 3000 ft suggests hydrocarbon did not migrate through this zone. The break at 3000 ft between zones 154 and 156 corresponds to the Cambrian-Precambrian unconformity. Sandstones are found on both sides of this unconformity, and there is no petrophysical evidence that this surface is a seal. Taken together, these data suggest that hydrocarbon migration, at least through zone 154 between about 3000 and about 13,000 ft, occurred prior to the deposition of the Cambrian sands of zone 156.

Referring now to FIG. 9, FIG. 9 shows the mass spectrum of collective inclusion volatiles from 16,000 ft in the well illustrated in FIG. 8. Hydrocarbons at least well out into the gasoline range are observed. Since inclusion gases are subject to the same thermal stresses experienced in the open-pore system and hydrocarbons are observed out into the gasoline range, indicating no thermal cracking, the data in FIG. 9 suggest the rocks in zone 150 did not reach catagenetic or breakdown temperatures. It is noted that this interpretation would be difficult or impossible using a display such as that of FIG. 6B.

EXAMPLE II

Subaerial Exposure Zones

Paleo-vadose zones, and therefore paleo-exposure zones, can be rapidly identified using automated fluid inclusion volatile analyses in accordance with the invention. Vadose zone sediments include all sediments above the water table during mineral formation. The pores in sediments in the vadose zone are occupied by a mixture of atmospheric air and water.

Paleo vadose zones are conventionally recognized through a combination of petrology and stable isotope chemical stratigraphy. Carbonates that form in the vadose zones have characteristic cements called "meniscus" and "pendant". Petrographic identification of these cements is positive evidence of paleo-vadose environments.

Also, vadose zones have characteristically light Carbon-isotope signatures. The isotopically light Carbon found in the vadose zone is derived from rotting vegetation. These data are used to define paleo-vadose zones. Although these techniques can be definitive they are very time consuming, and involve considerable sample preparation.

Cements that form around and between minerals in the vadose zone trap variable amounts of air and water in fluid inclusions. Petrographic identification of inclusions having variable amounts of air and water can therefore also be used to identify paleo-vadose zones. However, this technique is also extremely time consuming, and requires considerable sample preparation.

A rapid method of identifying paleo-vadose zones is by automated analyses of volatiles in fluid inclusions according to the invention.

Inclusions that form in vadose environments trap small amounts of air. A characteristic gas in air that does not occur in the subsurface is molecular oxygen, Argon, Xenon and the like, i.e., $O_2$, Ar, Xe. The autosampler/mass spectrometer system in accordance with the invention rapidly identifies those samples that contain these molecules in inclusions. Vadose zones that have been identified in this fashion, i.e., by the presence of molecular oxygen or Argon or Xenon in fluid inclusions, have been confirmed by petrographic and isotopic investigations.

Documenting paleo-vadose zones is important in exploration for oil and gas inasmuch as it documents paleo exposure zones. A regional study of paleo exposures can permit the delimitation of paleo-shore lines, as well as paleo topography, inasmuch as water tables follow topography. A knowledge of paleo topography can be used in exploration for reservoired hydrocarbons trapped along unconformities. Further, paleo exposure zones are often either zones of porosity enhancement or porosity destruction. Zones of porosity enhancement are potential reservoirs, zones of porosity destruction are potential seals. Hence, a method for rapidly and easily identifying paleo exposure zones in the subsurface provides great advantage to the oil and gas explorationist.

Referring now to FIG. 10, FIG. 10 shows the variation of argon content in the inclusions mass ratio 40/41+40 as function of depth. Argon has mass 40 and is somewhat masked by presence of adjacent hydrocarbon fragments. Hence, one of these fragments, such as MCR fragment ratio 41, is selected for comparison to remove to some extent effects of hydrocarbon from argon response at 40. Note the presence of two positive anomalies, zone 158 between 13,000 and 15,000 ft, and zone 160 between 8,500 and 9,500 ft. These zones are also found to show high abundances of nitrogen and molecular oxygen (logs not shown). Molecular oxygen is a gas only found at the earth's surface, and as such is a direct indicator of subaerial exposure. Nitrogen is the most abundant atmospheric gas, and argon is a diagnostic trace atmospheric gas. The dissolved argon, nitrogen, and oxygen contents of surficial waters are very low, especially compared to atmospheric abundances. These two argon-enriched inclusion zones can therefore be considered indicators of paleosubaerial exposure surfaces. The lower exposure zone 158 corresponds to the hydrocarbon seal (zone 152) indicated in FIG. 8. Therefore, this surface is indicated to be a sealing exposure zone. The argon-enriched inclusion zone 160 around 9000 ft has methane contents that are not noticeably different from the stratigraphically-higher and lower Precambrian sands (see FIG. 8). This zone is indicated to be a nonsealing exposure zone.

Independent evidence is obtained that suggests zones 158 and 160 are subaerial exposure surfaces. The lower zone 158 is composed of a red, fine-grained siltstone. The red color of this siltstone suggests an oxidized nature, consistent with it being an exposure zone. The fine-grained nature of this siltstone is also consistent with the sealing hypothesis. A core from the upper zone 160 was studied and described as an Eolian sequence, which is by definition a subaerial exposure zone. If these exposure zones are laterally extensive, then their inclusion signature will provide a stratigraphic time marker in the basin.

EXAMPLE III

Cambrian/Precambrian Unconformity Stratigraphic Marker

Referring now to FIG. 11, FIG. 11 shows variation in nitrogen relative to $CO_2$ in the well. A break or transition between two zones is indicated by reference numeral 162 at about 3000 ft, at the Cambrian-Precambrian unconformity. The Precambrian rocks in the zone below break 162 are enriched in nitrogen relative to the Cambrian rocks above break 162. This behavior is found repeatedly at Paleozoic-Precambrian unconformities. FIG. 12 shows the same pattern in another well at reference numeral 164.

Analyses of fluid inclusions in well cuttings appears to indicate the Paleozoic-Precambrian unconformity on the basis of nitrogen content—Precambrian sediments have nitrogen-enriched inclusions, and Paleozoic inclusions are nitrogen depleted, therefore providing a Precambrian stratigraphic marker. Without limiting the invention, this pattern hypothesized to be due to the explosion of life at the beginning of the Paleozoic. The accumulation of extremely large amounts of biomass resulted in the removal of nitrogen from the atmosphere, and subsequently a decrease of dissolved nitrogen in waters trapped in fluid inclusions. This may be a worldwide stratigraphic horizon.

EXAMPLE IV

Helium Precambrian Stratigraphic Marker

FIG. 13 shows variation of helium content of inclusions in the well. A measure of helium in the subsurface is obtained by using the ratio of 4/4+2. Both helium and deuterium contribute to the peak at 4; but only hydrogen contributes to the peak at 2. The abundance of deuterium varies with the abundance of hydrogen. Hence, the ratio 4/4+2 can be used to remove to some extent the effects of deuterium on the peak at 4. Note that the helium contents increase very rapidly in zone 166 below 13,000 ft. Similar variations are found in wells that tested the upper Precambrian in other wells worldwide. Helium contents of this magnitude have not been observed in analyses of younger rocks. In younger rocks that have helium in some inclusions, such stratigraphically-thick helium-enriched sections have not been observed. Detailed petrographic analyses of sandstones from the well shows no noticeable petrophysical change near the abrupt increase in helium content. Red sandstones having hematite cement occur above and below this helium transition. This helium marker, therefore, provides a Precambrian stratigraphic time marker.

Without limiting the invention, this change in helium content of the fluid inclusions is hypothesized to be a result of changing oxidation states of the earth's atmosphere. Helium-rich inclusions are hypothesized to occur in sediments deposited when the earth's atmosphere was sufficiently reducing so that uranium valence state was such as to render it relatively insoluble in water. Under these conditions, uranium would be deposited as detritus. Uranium varied with the original sediment could produce helium throughout time by radioactive decay. This helium could be trapped as fluid inclusions once liberated, or if small amounts of uranium were trapped as solid inclusions, the helium would be trapped in the same inclusion. Under more oxidizing atmospheric conditions, uranium would be soluble in water, and would not be deposited as detritus. Therefore, helium-rich inclusions would not be expected.

EXAMPLE V

Trapping Fault and Migration Identification

This EXAMPLE illustrates the use of fluid inclusion stratigraphy for identifying trapping and nontrapping faults.

Referring now to FIG. 14A, FIG. 14A represents a well 350 testing a simple fault trap. As illustrated the well has cross faults A and B (illustrated by arrows 352 showing relative movement of various strata 354) missing oil trapped in reservoirs R upthrown to fault A. It is not known whether fault A is a trapping fault.

Referring now to FIG. 14B, FIG. 14B illustrates a log display 356 of paraffin abundance in fluid inclusions as a function of depth along wellbore 350. The log display is smoothed and generalized for simplicity.

Between faults A and B, curve 356 shows there is a zone of relatively high paraffin content. The return to lower values of paraffin above fault A indicates that fault A is a trapping fault. The return to lower values of paraffin below fault B indicates fault B may be the migration pathway along which oil migrated into traps R.

EXAMPLE VI

Subtle Stratigraphic Traps

This EXAMPLE illustrates that fluid inclusion stratigraphy can be used for locating subtle stratigraphic traps within a formation. FIG. 15A is a structure contour map of the topographic top of a producing formation. Production wells #3, #4, #5 occur in the region. Ternary diagrams showing variations in fluid inclusion compositions for various wells in and around the field of FIG. 15A are shown in FIG. 15C. These ternary diagrams show the relative variations of masses 15 (methane), 44 ($CO_2$), and 41 (an oil fragment). The intensity of mass 41 was multiplied by a factor of 10 prior to plotting Note that all the producing wells #3, #4, #5 in the field show very similar fluid inclusion composition patterns. A down-dip dryhole #6 shows fluid inclusion compositions also very similar to those found in the field. Two wells #1, #2 north of a barrier to hydrocarbon migration line 238 have inclusion compositions distinctly different from those of producing wells #3, #4, #5 in the field, but similar to each other. One of these two wells produce water updip to oil.

The field could have been located using fluid inclusion analyses of the three dryholes just mentioned.

The similarity of the inclusion data for wells #1 and #2 provides no encouragement for continued exploration in between them. However, the marked difference in fluid inclusion composition between these two wells and the well #6 indicates some sort of subsurface chemical compartmentalization, suggesting the possibility of a trap between these wells. Exploration between the wells #6 and wells #1 and #2 would have resulted in the discovery of the field.

Referring now to FIG. 15B, FIG. 15B illustrates percent $CO_2$ to $CO_2$ plus methane in inclusions for wells #1 through #6. Wells #1 and #2 are similar to one another but differ from wells #3, #4, and #5 which are self-similar, and from well #6. If during prediscovery, wells #1, #2, and #6 had been drilled and found nonproductive (as indicated by stippling in FIG. 15B), fluid inclusion analysis in accordance with the invention would have suggested that a potential trap existed between the due to the contrast in $CO_2$ inclusion contents. Subwells sequent drilling between wells #2 and #6 at virtually any location would have resulted in discovery of the field.

FIG. 15D illustrates ternary diagrams of FIG. 15C displayed relative to formation map 15a.

EXAMPLE VII

Fluid Inclusion Stratigraphy

Thirteen complete wells are analyzed in an area. A repetitive fluid inclusion stratigraphy i.e., different zones each having characteristic fluid inclusion compositions, is seen in many of these wells. For example, by considering the variation of paraffins relative to methane, a zone of low paraffin abundances are found shallow and deep, and a zone of abundant paraffins is found at some intermediate depths. The paraffin-rich zone is several thousand feet thick. Porous sands are found generally to occur within, above, and below these paraffinenriched zones. Thus, the paraffin-enriched zones are not coincident with normal stratigraphy from well to well. The tops and bottoms of these paraffin-enriched inclusion zones are found usually to be fault-bounded. In wells having oil shows, the "oily" inclusion zones are found to extend thousands of feet below the deepest reported show.

The consistency of these blocky inclusion patterns from well to well argues for a general genetic process.

The bottom of these zones is determined to mark the basal hydrocarbon migration pathway in that well, and the top to mark a barrier to hydrocarbon migration. It is assumed that vertical migration may occur within these zones.

Preliminary data show that the basal migration pathway becomes shallower both to the east and west of the field. These data suggest the specific fault systems may be the main conduits in the field. The basal migration pathway may be predictive as to the maximum productive depth in an area.

EXAMPLE VIII

Determining Direction of Oil Accumulations By Measuring Diffused Aromatics in Fluid Inclusions All of the various aspects of the invention relate at least in part to stratigraphic mapping of the subsurface using composition data of collective fluid inclusion volatiles. The heterogeneous mixtures of gases, as has been shown, are a powerful tool for mapping and interpreting the subsurface—a tool which permits mapping chemical compartmentalization independently of knowledge of geological structure in the earth, but which greatly assist in interpreting geological structure.

Aromatics are known to diffuse outwardly from oil accumulations forming an abundance gradient. Fluid inclusions are formed on an ongoing basis. This suggests that measurement of fluid inclusion aromatics can be used to identify the direction of oil accumulation.

For a known oil accumulation analysis using the invention determined toluene versus toluene plus $CO_2$ ratios (representative of abundance of toluene). The resulting data show an increase in the toluene/(toluene plus $CO_2$) ratio in the direction of the oil accumulation.

This EXAMPLE illustrates usefulness of the invention for identifying direction of oil accumulations.

EXAMPLE IX

Reservoir and Fault Detection From Fluid Inclusion Compositions

This EXAMPLE illustrates the use of fluid inclusion composition zones for mapping a particular field.

Fluid inclusion composition data from core samples and drill cuttings from five wells in an area are used to map a field in accordance with the invention.

Detailed sampling of core (one sample per foot) from productive and nonproductive thrust sheets allows plotting of fluid inclusion compositional data where variations in lithology and porosity are well-known. Referring to FIG. 16A, FIG. 16A illustrates a ternary plot in accordance with the invention of $CO_2/CH_4/H_2S$ showing characteristic composition patterns for porous sandstone, shale and nonporous sandstone.

FIG. 16B illustrates a ternary plot of $CO_2/CH_4/H_2S$ showing characteristic inclusion compositions for productive and nonproductive thrusts. These data indicate adequate fluid inclusion chemical compartmentalization for using fluid inclusion analysis in this field for distinguishing these geological features.

Referring now to FIG. 16C, FIG. 16C illustrates a log display in accordance with the invention of $H_2$ (normalized relative to $CO_2$) as a function of depth. The high $H_2$ zones 270, 272, 274 are found to occur on thrust sheets with good shows or producible gas reservoirs. The $H_2$ plots do not distinguish between economic and uneconomic gas accumulations in this field.

Referring now to 16D, FIG. 16D illustrates variation in $CO_2/CO_2$ plus $CH_4$ for a well. The $CO_2$ anomalies 276, 278, 280, 282, 284 are negative and in sandstone intervals containing porous zones. By identifying updip porous zones, new zones are identified for production testing. This illustrates use of the invention for locating porosity zones.

Referring now to FIG. 16E, FIG. 16E illustrates variations in helium/(helium plus hydrogen). Positive helium anomalies 286, 288, 290, 292, and 294 are found by comparison with seismic data, to occur in thrust fault zones. This illustrates use of the invention to aid in identifying thrust zones.

The positive helium anomalies occurring at thrust fault zones occur whether or not the thrust fault is productive.

This EXAMPLE indicates that for this field, hydrogen sulfide anomalies occur in productive thrust sheets, carbon dioxide anomalies occur in porous sandstone, and helium anomalies occur in thrust salts.

These characteristic fluid inclusion signatures can be used to map these zones in other wells in the field and may be generalizable to other fields.

EXAMPLE X

Mapping Structural Features from Fluid Inclusion Composition Data

This EXAMPLE illustrates use of fluid inclusion composition zones for identifying structural features in a field.

Seven wells in the study area were selected for analysis and ternary plots of various elements are found to distinguish from updip platform, downdip lagoonal limestone, and porous rock (gas or water filled).

Fluid inclusions in updip platform rocks have relatively high saturations of methane.

Fluid inclusions in bitumen-filled foreslope facies can easily be distinguished as being enriched with toluene and hydrogen sulfide ($H_2S$).

Fluid inclusions in the lagoonal limestones are enriched in carbon dioxide ($CO_2$) and depleted in methane.

Fluid inclusion in late stage calcspars are depleted in methane, and enriched in $H_2$ or HC1 plus (more saline).

Using these characteristic compositions, the field can be mapped as a function of the identified zones.

In the course of making the invention in its various aspects, many problems were solved.

A system was developed for individually crushing and analyzing inclusion contents of a plurality of samples. Crushing of samples was made to occur in a continuously pumped vacuum to speed processing and to ensure that freshly released volatiles absorbed as little as possible to surfaces exposed by crushing. There was developed means for keeping a plurality of samples separate, while crushing each of them separately under a vacuum. For efficiency, a system was developed for using a smaller number of crusher means for crushing samples than there were samples and also means for moving samples into position for crushing. The system was made to be sturdy enough for repeated use. Released volatiles were quickly delivered to analysis means for producing an adequate record of most all of the elements and compounds present for chemical inclusion zone mapping of the subsurface. Analytical instrumentation itself was developed to detect the low amounts of trace elements and compounds present in fluid inclusions which, as described above, confer many significant benefits on oil and gas explorationists. The large amounts of resulting composition data were stored in retrievable form. The resulting data representative of heterogeneous mixtures of elements and compounds released from myriad inclusions in each sample were processed and interpreted and various displays by depth and areal location were developed to assist in interpretation and use of the data.

Using the invention in its various aspects has permitted analysis and interpretation of fluid inclusion compositions in three dimensions in the earth's crust, that is, in both a vertical and lateral sense. Fluid inclusion stratigraphy of sedimentary formations has been subject to such difficulties in obtaining adequate data for the numerous microscopic (typically <10 microns) fluid inclusions present that it has not previously been seriously attempted or contemplated by others.

Use of chemical fluid inclusion mapping of the subsurface has permitted mapping of oil/gas migration pathways, placing timing constraints on oil/gas migration, demonstrating multiple episodes of oil/gas migration, locating seals, locating faults, demonstrating fluid migration along faults, locating unconformities, locating paleo-exposure surfaces (paleovadose zones), estimating thermal exposure (hydrocarbon maturation and catagenesis), and providing time horizons (stratigraphic time markers) in various sediments. Many other advantages can also be obtained.

Fluid inclusion stratigraphy in accordance with the invention is a rapid technique based on the analyses of hundreds or thousands of samples per day for fluid inclusion volatile composition. It is this speed and ease of data acquisition that makes these types of studies possible.

The invention has been described in terms of preferred embodiments and specific applications but is not

What is claimed is:

1. Apparatus, including controller means, for releasing, delivering, and analyzing composition of a plurality of fluid inclusion volatiles samples comprising:
    releasing means for impacting and deforming a sedimentary rock sample effective for releasing a fluid inclusion volatiles sample therefrom, the releasing means comprising an evacuable chamber, impacting means within the evacuable chamber for impacting a positioned semimentary rock sample and releasing a collective fluid inclusion volatiles sample from a myriad of fluid inclusions therein; and positioning means within the evacuable chamber for supporting a plurality of sedimentary rock samples and positioning one of the plurality of sedimentary rock samples relative to the impacting means as the positioned one of the plurality of sedimentary rock samples;
    analytical means for determining the chemical composition of the fluid inclusion volatiles sample as it is being released, the analytical means comprising:
        an analyzer for analyzing the chemical composition of collective fluid inclusion volatiles samples while being released, each volatiles sample being a heterogeneous mixture of volatiles released from the myriad fluid inclusions in the rock sample, wherein the heterogeneous mixture of volatiles analyzed comprise hydrocarbons having more than one carbon atom, the analyzer comprising:
            a plurality of mass spectrometric means for determining mass to charge ratio responses of each collective fluid inclusions volatiles sample, wherein the mass spectrometric means operate concurrently and each mass spectrometric means is configured to sample a specific set of mass to charge ratio responses;
            means for causing each of the plurality of mass spectrometric means to scan its set of mass to charge ratio responses a multiplicity of times during a period of time while each collective fluid inclusion volatiles sample is being provided to mass spectrometric means;
            means for summing mass to charge ratio responses on a mass to charge ratio by mass to charge ratio basis for all of the multiplicity of scans for each rock sample's collective fluid inclusions volatiles sample;
            means for storing summed mass to charge ratio responses as a record of the composition of collective fluid inclusions volatiles sample for each sedimentary rock sample;
        delivery means for delivering the fluid inclusion volatiles sample from releasing means to analytical means as it is being released; and
        controller means for causing the releasing means to sequentially and individually release the collective fluid inclusions volatiles sample from each of the plurality of sedimentary rock samples and for causing each collective fluid inclusion volatiles sample to be sequentially and individually analyzed by the analytical means, wherein the controller means comprises:
            means for generating a positioning signal causing the positioning means to position one of the plurality of sedimentary rock samples relative to the impacting means for impacting the positioned rock sample;
            means for generating an impacting signal for causing impacting means to impact the positioned rock sample;
        means for generating an analyzing signal for causing the analytical means to analyze the composition of gases in the evacuable chamber including collective fluid inclusion volatile; and
            means for effecting sequential operation of the previously defined means for each of the plurality of rock samples in the evacuable chamber.

2. The apparatus of claim 1 wherein the controller means further comprises:
    means for generating an analyzing signal for causing the analytical means to analyze the composition of background gas in the evacuated chamber prior to generating the impacting signal for causing the impacting means to impact a positioned rock sample and release a collective fluid inclusion volatiles sample therefrom, and subsequent to generating a positioning signal causing positioning means to position one of the plurality of sedimentary rock samples relative to the impacting means for impacting the positioned rock sample.

3. The apparatus of claim 1 wherein the means for effecting sequential operation comprises:
    means for determining whether all samples of the plurality of sedimentary rock samples have been impacted by the impacting means;
    means responsive to means for determining for generating a positioning signal for positioning a further rock sample relative to impacting means effective for the impacting means impacting the further rock sample;
    means for generating an impacting signal for causing the impacting means to impact the further rock sample; and
    mean for terminating sequential operation responsive to a condition that all samples of the plurality of sedimentary rock samples have been impacted by the impacting means.

4. The apparatus of claim 3 wherein the means for effecting sequential operation further comprises:
    means for generating an analyzing signal for causing the analytical means to analyze the composition of gas in the evacuated chamber prior to and also subsequent to generating a signal for causing impacting means to impact sedimentary rock sample and release a collective fluid inclusion volatiles sample therefrom.

5. The apparatus of claim 4 wherein the analytical means further comprises:
    means for generating analysis data, and wherein the controller means further comprises:
    means for storing analysis data generated prior to and subsequent to generating an impacting signal for causing the impacting means to impact the sedimentary rock sample.

6. A controller for controlling apparatus comprising an evacuable chamber, impacting means within the evacuable chamber for impacting positioned sedimentary rock samples, and positioning means within the evacuable chamber supporting a plurality of rock samples and for positioning one of the plurality of sedimentary rock samples relative to the impacting means comprising:
  means for causing positioning means to position one of the plurality of samples relative to the impacting means as the positioned one of the plurality of sedimentary rock samples effective for impacting the positioned rock sample;
  means for generating an impacting signal for causing impacting means to impact the positioned rock sample;
  means for generating an analyzing signal for causing an analyzer to analyze the chemical composition of gases including released volatiles in the evacuable chamber, wherein said released volatiles comprise hydrocarbon having more than one carbon atom and the analyzer comprises a plurality of mass spectrometric means operating concurrently with each mass spectrometric means being configured to sample a specific set of mass to charge ratio responses; and
  means for effecting sequential operation of the previously defined means for the plurality of rock samples in the evacuated chamber.

7. The controller of claim 6 further comprising:
  means for determining whether all samples of the plurality of rock samples have been impacted by the impacting means and a collective fluid inclusion volatiles sample released therefrom;
  means responsive to means for determining for generating a positioning signal for positioning a further one of the plurality of sedimentary rock samples as the positioned rock sample relative to the impacting means as the positioned one of the plurality of sedimentary rock samples effective for impacting means impacting the positioned rock sample;
  means for generating an impacting signal for causing the impacting means to impact the positioned rock sample; and
  means for terminating sequential operation response to a condition that all samples of the plurality of rock samples have been impacted by the impacting means.

8. The controller of claim 6 wherein the means for generating analyzing signal for causing an analyzer to analyze the chemical composition of gases comprises:
  means for generating a signal for causing the plurality of mass spectrometric means to analyze the composition of gases in the evacuable chamber prior to and also subsequent to generating an impacting signal for causing the impacting means to impact the rock sample.

9. The controller of claim 8 wherein the analyzer to analyze the chemical composition of gases including released volatiles in the evacuable chamber comprises:
  means for generating analysis data, and the controller further comprising:
  means for storing analysis data generated prior to and subsequent to generating an impacting signal for causing the impacting means to impact the rock sample.

10. The controller of claim 8 wherein the analyzer to analyze the chemical composition of gases including released volatiles in the evacuable chamber comprises:
  means for generating analysis data generation, and the controller further comprising:
  means for effecting a preliminary reduction of analysis data for fluid inclusions volatiles released from each separate rock sample by removing from the analysis data of gas present in the evacuated chamber subsequent to impacting each separate rock sample, the effect of gas present in the evacuated chamber prior to impacting each separate rock sample.

11. A method of controlling apparatus comprising an evacuable chamber, impacting means within the evacuable chamber for impacting positioned rock samples, positioning means within the evacuable chamber supporting a plurality of rock samples and for positioning each one of the plurality of separate rock samples relative to the impacting means, and an analyzer connected to the evacuable chamber for receiving released collective fluid inclusion volatiles therefrom for determining the chemical composition thereof, the method comprising:
  generating a positioning signal for causing one of the plurality of rock samples to be positioned relative to the impacting means as the positioned one of the plurality of rock samples effective for the impacting means impacting the rock sample;
  generating an impacting signal for causing the impacting means to impact the positioned rock sample;
  generating an analyzing signal for causing the analyzer to determine the chemical composition for collective fluid inclusion volatiles released by crushing, wherein said analyzer comprises a plurality of mass spectrometric means operating concurrently with each mass spectrometric means being configured to sample a specific set of mass to charge ratio response and said collective fluid inclusion volatiles comprise hydrocarbon having more than one carbon atom; and
  repeating the preceding three steps for each of the plurality of rock samples within the evacuated chamber.

12. The method of claim 11 wherein the repeating step comprises:
  determining whether all samples of the plurality of rock samples have been impacted by the impacting means;
  responsive to a condition that a collective fluid inclusion volatiles sample has not been released from all of the plurality of rock samples and the chemical composition thereof determined;
  generating a positioning signal for positioning a further one of the plurality of rock sample relative to the impacting means as the positioned one of the plurality of sedimentary rock samples effective for the impacting means impacting the positioned rock sample;
  generating an impacting signal for causing the impacting means to impact the positioned rock sample;
  generating an analyzing signal for causing the analyzer to determine the chemical composition for collective fluid inclusion volatiles released by crushing; and
  terminating the repeating step responsive to a condition that all samples of the plurality of rock samples have been impacted by the impacting means.

13. The method of claim 11 wherein the step of generating an analyzing signal for causing the analyzer to determine the chemical composition comprises:
  generating an analyzing signal for causing the analyzer to determine composition of gas in the evacuated chamber prior to and also subsequent to generating an impacting signal for causing the impacting means to impact the positioned rock sample.

14. The method of claim 13 wherein the step of generating an analyzing signal for causing the analyzer to determine the chemical composition comprises:

generating a signal for analysis data generation, and the method further comprising:

storing analysis data generated prior to and subsequent to generating an impacting signal for causing the impacting means to the impact rock sample.

15. The method of claim 13 wherein the step of generating an analyzing signal for causing the analyzer to determine the chemical composition comprises:

generating a signal for analysis data generation, and the method further comprising:

effecting a preliminary reduction of analysis data for fluid inclusion volatiles released from each separate rock sample by removing from the analysis data of gas present in evacuated chamber subsequent to impacting each separate rock sample, the effect of gas present in evacuated chamber prior to implanting each separate rock sample.

* * * * *

UNITED STATES PATENT AND TRADEMARK OFFICE
CERTIFICATE OF CORRECTION

PATENT NO. : 5,286,651
DATED : February 15, 1994
INVENTOR(S) : Michael P. Smith

It is certified that error appears in the above-indentified patent and that said Letters Patent is hereby corrected as shown below:

| Col. | Line | | | |
|------|------|---|---|---|
| 14 | 14 | "the reading were" | should read | --the readings were-- |
| 16 | 34 | "HCl" | should read | --HCl-- |
| 16 | 35 | "$H_2$" | should read | --$H_2S$-- |
| 16 | 37 | "$H_2$" | should read | --$H_2S$-- |
| 19 | 43 | "(methand)" | should read | --(methane)-- |
| 25 | 43 | "line 238" | should read | --line 239-- |
| 25 | 67 | "between the due" | should read | --between the wells due-- |
| 25 | 68 | "Subwells sequent" | should read | --Subsequent-- |

UNITED STATES PATENT AND TRADEMARK OFFICE
CERTIFICATE OF CORRECTION

PATENT NO. : 5,286,651
DATED : February 15, 1994
INVENTOR(S) : Michael P. Smith

It is certified that error appears in the above-indentified patent and that said Letters Patent is hereby corrected as shown below:

| Col. | Line | |
|---|---|---|
| 27 | 26 | "$H_2$" should read --$H_2S$-- |
| 27 | 28 | "$H_2$" should read --$H_2S$-- |
| 27 | 30 | "$H_2$" should read --$H_2S$-- |
| 30 | 10 | "inclusion volatile;" should read --inclusion volatiles;-- |
| 31 | 39 | "operation response to" should read --operation responsive to-- |
| 32 | 32 | "charge ratio response" should read --charge ratio responses-- |

Signed and Sealed this

Seventeenth Day of October, 1995

Attest:

BRUCE LEHMAN

*Attesting Officer*     *Commissioner of Patents and Trademarks*